United States Patent
Davidson et al.

(10) Patent No.: US 11,413,417 B2
(45) Date of Patent: Aug. 16, 2022

(54) PATIENT INTERFACE

(71) Applicant: RESMED PTY LTD, Bella Vista (AU)

(72) Inventors: Aaron Samuel Davidson, Sydney (AU); Rupert Christian Scheiner, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 466 days.

(21) Appl. No.: 16/498,995

(22) PCT Filed: Mar. 29, 2018

(86) PCT No.: PCT/AU2018/050289
§ 371 (c)(1),
(2) Date: Sep. 27, 2019

(87) PCT Pub. No.: WO2018/176094
PCT Pub. Date: Oct. 4, 2018

(65) Prior Publication Data
US 2020/0054850 A1 Feb. 20, 2020

Related U.S. Application Data

(60) Provisional application No. 62/480,059, filed on Mar. 31, 2017.

(51) Int. Cl.
*A61M 16/06* (2006.01)
*A61M 16/00* (2006.01)
*A61M 16/10* (2006.01)

(52) U.S. Cl.
CPC .... *A61M 16/0666* (2013.01); *A61M 16/0622* (2014.02); *A61M 16/0683* (2013.01);
(Continued)

(58) Field of Classification Search
CPC .............. A61M 16/06; A61M 16/0605; A61M 16/0616; A61M 16/0622; A61M 16/0633; A61M 16/0638
See application file for complete search history.

(56) References Cited

U.S. PATENT DOCUMENTS

| 4,782,832 A | 11/1988 | Trimble et al. |
| 4,799,477 A * | 1/1989 | Lewis .................. A62B 18/025 128/206.26 |

(Continued)

FOREIGN PATENT DOCUMENTS

| CN | 103961775 A | 8/2014 |
| CN | 106488784 A | 3/2017 |

(Continued)

OTHER PUBLICATIONS

"Respiratory Physiology", by John B. West, Lippincott Williams & Wilkins, 9th edition published 2012, 8 pages.

(Continued)

*Primary Examiner* — Michael J Tsai
(74) *Attorney, Agent, or Firm* — Nixon & Vanderhye P.C.

(57) ABSTRACT

A seal-forming structure for a patient interface may include a patient-contacting surface configured to engage the patient's facial skin to form a seal; a posterior opening formed in the patient-contacting surface, the posterior opening configured to provide the flow of air at said therapeutic pressure to the patient's nares; and a support structure extending from the patient contacting surface to an interior surface of the seal-forming structure, the support structure and the interior surface forming a continuous loop, wherein the patient interface is configured to allow the patient to breath from ambient through their mouth in the absence of a flow of pressurised air through the plenum chamber inlet port, or the patient interface is configured to leave the patient's mouth uncovered.

18 Claims, 33 Drawing Sheets

(52) U.S. Cl.
CPC ....... *A61M 16/0069* (2014.02); *A61M 16/022* (2017.08); *A61M 16/109* (2014.02); *A61M 2202/0208* (2013.01); *A61M 2205/50* (2013.01); *A61M 2210/0618* (2013.01)

(56) References Cited

U.S. PATENT DOCUMENTS

| | | | |
|---|---|---|---|
| 4,834,085 A * | 5/1989 | Webster, II | A61M 16/0048 |
| | | | 128/202.29 |
| 4,944,310 A | 7/1990 | Sullivan | |
| 5,687,715 A | 11/1997 | Landis | |
| 6,135,109 A * | 10/2000 | Blasdell | A61M 16/06 |
| | | | 128/206.28 |
| 6,532,959 B1 | 3/2003 | Berthon-Jones | |
| 6,581,594 B1 | 6/2003 | Drew et al. | |
| 7,007,696 B2 * | 3/2006 | Palkon | A61M 16/0633 |
| | | | 128/206.26 |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,887,728 B2 * | 11/2014 | Boussignac | A61M 16/0622 |
| | | | 128/201.24 |
| 2005/0199242 A1 * | 9/2005 | Matula | A61M 16/0816 |
| | | | 128/207.18 |
| 2009/0044808 A1 | 2/2009 | Guney Memduh et al. | |
| 2009/0050144 A1 | 2/2009 | Pierce et al. | |
| 2009/0050156 A1 | 2/2009 | Ng et al. | |
| 2010/0000534 A1 | 1/2010 | Kooij et al. | |
| 2011/0247625 A1 * | 10/2011 | Boussignac | A61M 16/0447 |
| | | | 128/207.18 |
| 2012/0266890 A1 * | 10/2012 | Baecke | A61M 16/125 |
| | | | 128/207.13 |
| 2014/0196720 A1 | 7/2014 | Eury | |
| 2015/0352306 A1 | 12/2015 | Scheiner et al. | |
| 2016/0082214 A1 | 3/2016 | Barlow et al. | |
| 2016/0296720 A1 | 10/2016 | Henry et al. | |
| 2018/0256843 A1 | 9/2018 | Eves et al. | |
| 2019/0022343 A1 | 1/2019 | Kooij et al. | |
| 2019/0125996 A1 | 5/2019 | Davidson et al. | |

FOREIGN PATENT DOCUMENTS

| | | |
|---|---|---|
| WO | 98/004310 | 2/1998 |
| WO | 98/034665 | 8/1998 |
| WO | 00/078381 | 12/2000 |
| WO | 2004/073778 | 9/2004 |
| WO | 2005/063328 | 7/2005 |
| WO | 2006/074513 | 7/2006 |
| WO | 2006/130903 | 12/2006 |
| WO | 2009/052560 | 4/2009 |
| WO | 2010/131189 | 11/2010 |
| WO | 2010/135785 | 12/2010 |
| WO | 2011/022779 A1 | 3/2011 |
| WO | 2011/121463 A1 | 10/2011 |
| WO | 2012/171072 | 12/2012 |
| WO | 2013/020167 | 2/2013 |
| WO | 2013/170290 A1 | 11/2013 |
| WO | 2014/015382 A1 | 1/2014 |
| WO | 2014/110626 | 7/2014 |
| WO | 2015/070289 | 5/2015 |
| WO | 2015/196255 | 12/2015 |
| WO | 2016/032343 | 3/2016 |
| WO | 2016/149769 | 9/2016 |
| WO | 2017/042717 A1 | 3/2017 |
| WO | 2017/185140 | 11/2017 |

OTHER PUBLICATIONS

International Preliminary Report dated Mar. 20, 2019 issued in PCT/AU2018/050289. 175 pages.
International Search Report for PCT/AU2018/050289 dated Jul. 27, 2018, 5 pages.
Written Opinion of the ISA for PCT/AU2018/050289 dated Jul. 27, 2018, 8 pages.
Office Action dated Oct. 11, 2021 issued in Chinese Application No. 201880028656.0 with English translation (11 pages).
Extended European Search Report dated Dec. 17, 2019 issued in European Application No. 18776653.0 (9 pages).
Office Action dated Jan. 11, 2022 issued in Japanese Application No. 2019-553372 with English translation (11 pages).
Notification of Grant dated May 20, 2022 issued in CN Application No. 201880028656.0 (4 pages).

* cited by examiner

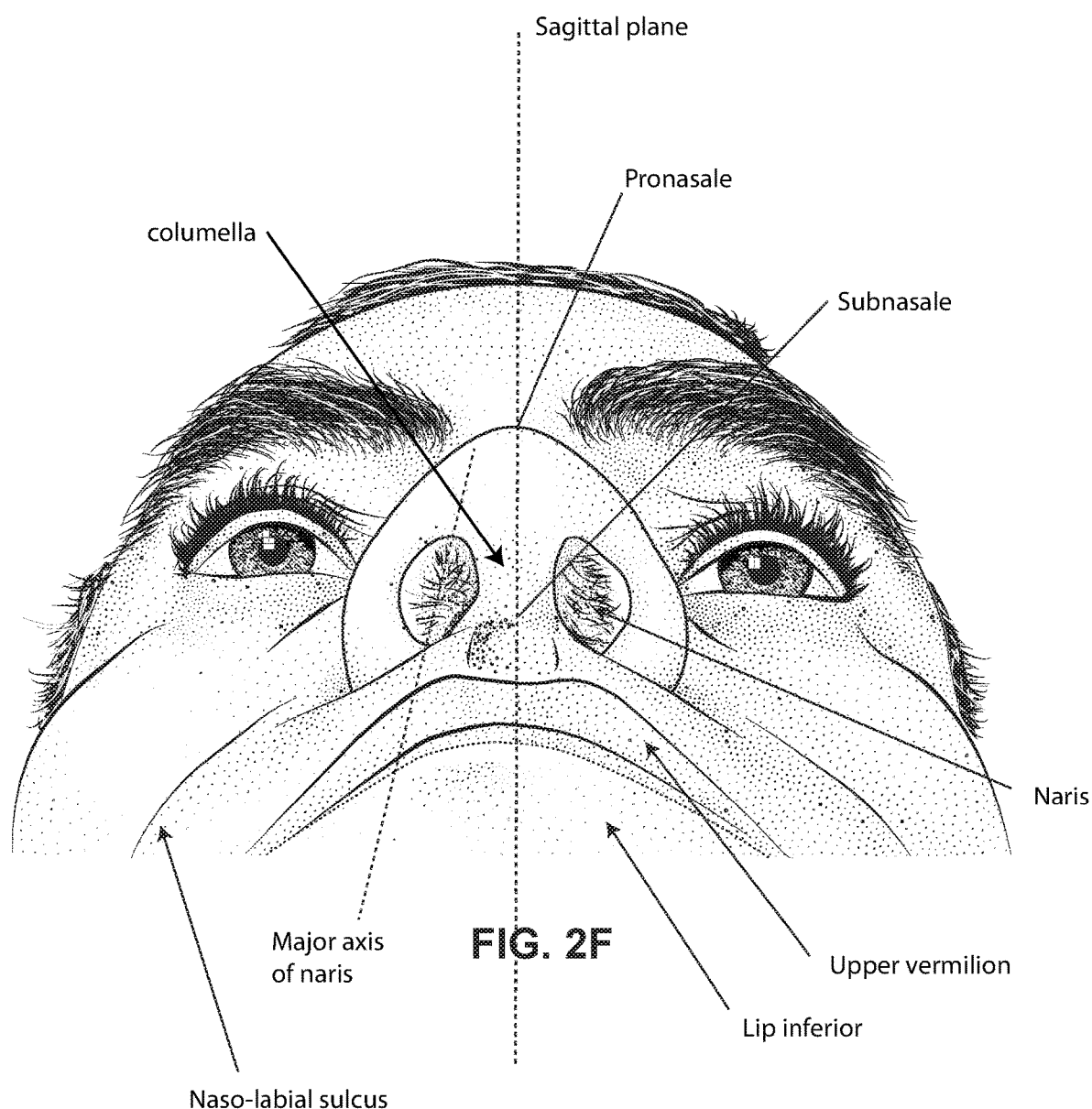

Relatively Large Positive Curvature

Relatively Small Positive Curvature

Zero Curvature

Relatively Small Negative Curvature

Relatively Large Negative Curvature

Copyright 2015 ResMed Limited

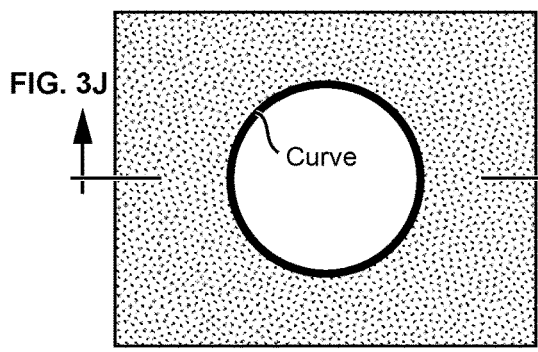
FIG. 3I
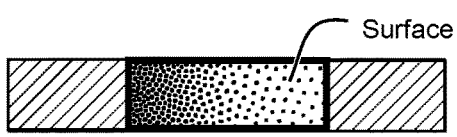
FIG. 3J
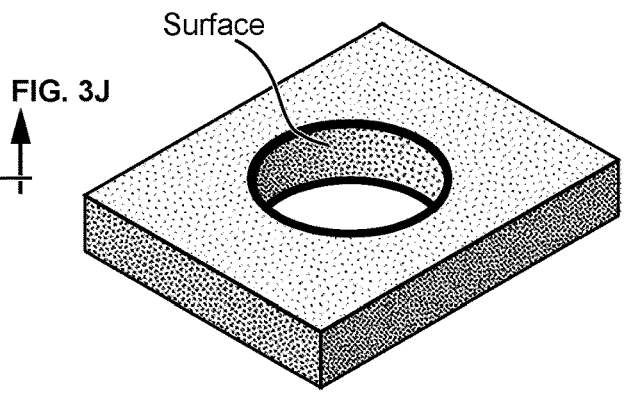
FIG. 3K
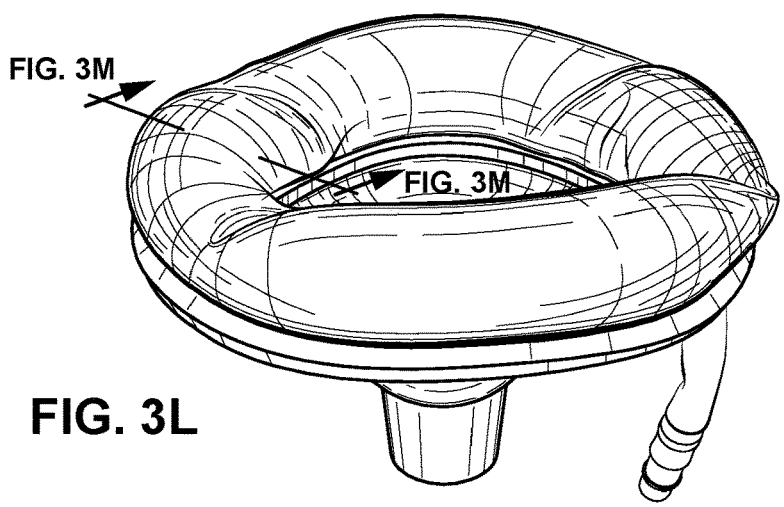
FIG. 3L
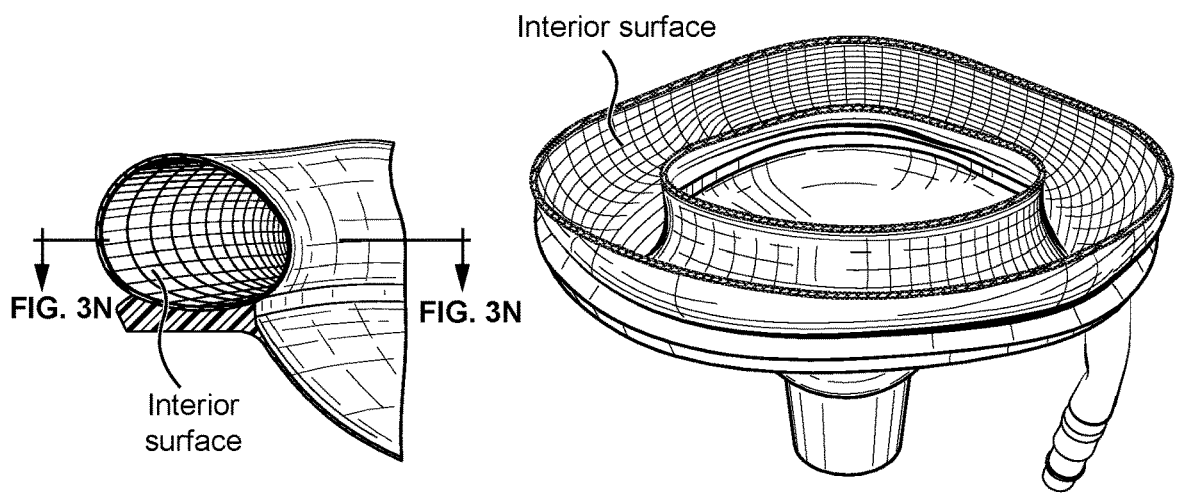
FIG. 3M     FIG. 3N

Left-hand rule

Right-hand rule

Left ear helix

Right-hand helix
Right-hand positive

Right ear helix

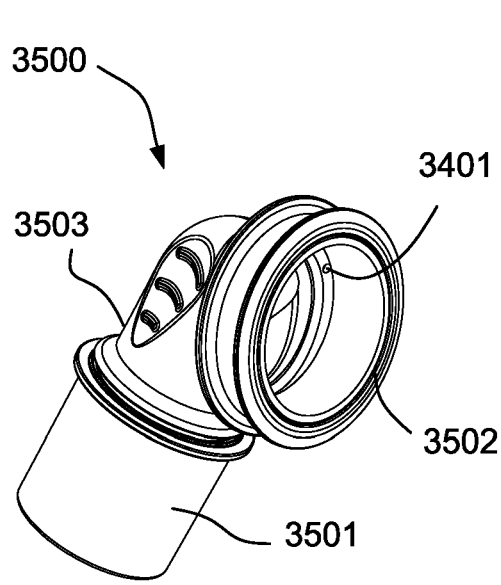
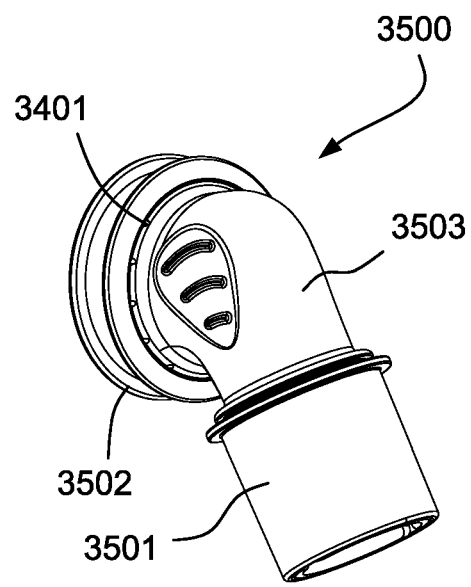
FIG. 8A              FIG. 8B
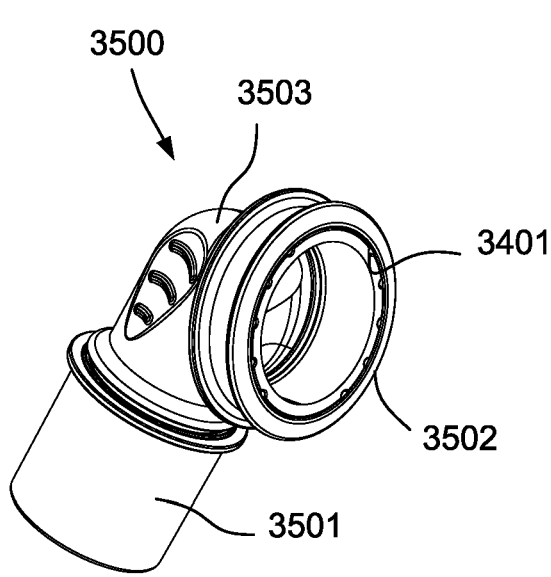
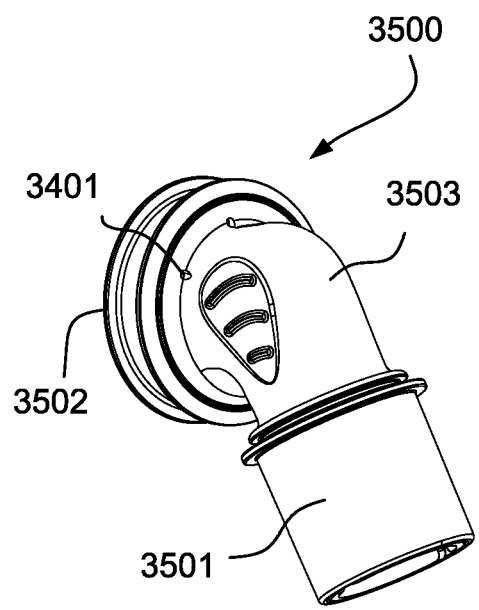
FIG. 9A              FIG. 9B

PATIENT INTERFACE

1 CROSS-REFERENCE TO RELATED APPLICATIONS

This application is the U.S. national phase of International Application No. PCT/AU2018/050289 filed Mar. 29, 2018 which designated the U.S. and claims the benefit of U.S. Provisional Application No. 62/480,059, filed Mar. 31, 2017, the entire contents of each of which are hereby incorporated by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

| Table of noise of prior masks (ISO 17510-2: 2007, 10 cmH$_2$O pressure at 1 m) | | | | |
|---|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |

-continued

Table of noise of prior masks (ISO 17510-2:
2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology is directed to a seal-forming structure for a patient interface that is configured to form a seal with the patient's nares and the seal-forming structure comprises a support structure forming a continuous loop with an interior surface of the seal-forming structure, the loop structure supporting a superior portion of a patient contacting surface of the seal-forming structure, and the superior portion of the patient contacting surface having a single layer that is not supported by an undercushion.

An aspect of the present technology is directed to a patient interface that comprises: a plenum chamber pressurisable to a therapeutic pressure of at least 6 cmH₂O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered, wherein the seal-forming structure further comprises a patient-contacting surface configured to engage the patient's facial skin to form a seal and a posterior opening formed in the patient-contacting surface, the posterior opening configured to provide the flow of air at said therapeutic pressure to the patient's nares, and wherein the seal-forming structure includes a support structure extending from a first location on the patient contacting surface to a second location on an interior surface of the seal-forming structure, the support structure and the interior surface forming a continuous loop.

In examples, (a) the seal-forming structure may comprise an anterior opening formed in a non-patient contacting surface and an anterior tie that spans the anterior opening, and a first end of the support structure may be connected to the anterior tie, (b) the seal-forming structure may comprise an edge bounding the posterior opening in the patient contacting surface, and a second end of the support structure may be connected to the patient contacting surface at a superior region of the edge, (c) the seal-forming structure may comprise an undercushion that supports the patient contacting surface, (d) an inferior portion of the seal-forming structure may include the undercushion and a superior portion of the seal-forming structure may not include the undercushion, (e) the support structure may have a length in an undeformed state that is greater than a linear distance from the first location to the second location, (f) the support structure may be configured to be positioned adjacent to or in contact with the patient's columella during use, (g) the support structure may be curved along a longitudinal axis of the support structure in an undeformed state, (h) the support structure may have a different thickness than the patient-contacting surface, (i) the support structure may be thicker than the patient-contacting surface, (j) the support structure may not extend completely across the posterior opening, (k) the seal-forming structure may at least partly form a gas chamber, and in an undeformed state the support structure may extends into the gas chamber, (l) the support structure may have a variable thickness in a longitudinal direction, (n) the support structure may have an increased thickness adjacent the first location and/or the second location, (n) a portion of the support structure may be curved away from the patient's nose along a longitudinal axis of the support structure in an undeformed state, and/or (o) the undercushion may be structured to only support the patient contacting surface against the patient's lip superior.

An aspect of the present technology is directed to a seal-forming structure for a patient interface, the seal-forming structure constructed and arranged to form a seal with a region of the patient's face surrounding an entrance to the patient's airways, the seal-forming structure constructed and arranged to maintain a therapeutic pressure of at least 6 cmH2O above ambient air pressure in a plenum chamber throughout the patient's respiratory cycle in use. The seal-forming structure comprises: a patient-contacting surface configured to engage the patient's facial skin to form a seal; a posterior opening formed in the patient-contacting surface, the posterior opening configured to provide the flow of air at said therapeutic pressure to the patient's nares; and a support structure extending from a first location on the patient contacting surface to a second location on an interior surface of the seal-forming structure, the support structure and the interior surface forming a continuous loop, wherein the patient interface is configured to allow the patient to breath from ambient through their mouth in the absence of a flow of pressurised air through the plenum chamber inlet port, or the patient interface is configured to leave the patient's mouth uncovered.

In examples, (a) the seal-forming structure may comprise an anterior opening formed in a non-patient contacting surface and an anterior tie that spans the anterior opening, and a first end of the support structure may be connected to the anterior tie, (b) the seal-forming structure may comprise an edge bounding the posterior opening in the patient contacting surface, and a second end of the support structure may be connected to the patient contacting surface at a superior region of the edge, (c) the seal-forming structure may comprise an undercushion that supports the patient contacting surface, (d) an inferior portion of the seal-forming structure may include the undercushion and a superior portion of the seal-forming structure may not include the undercushion, (e) the support structure may have a length in an undeformed state that is greater than a linear distance from the first location to the second location, (f) the support structure may be configured to be positioned adjacent to or in contact with the patient's columella during use, (g) the support structure may be curved along a longitudinal axis of the support structure in an undeformed state, (h) the support structure may have a different thickness than the patient-contacting surface, (i) the support structure may be thicker than the patient-contacting surface, (j) the support structure may not extend completely across the posterior opening, (k) the seal-forming structure may at least partly form a gas chamber, and in an undeformed state the support structure may extends into the gas chamber, (l) the support structure may have a variable thickness in a longitudinal direction, (n) the support structure may have an increased thickness adjacent the first location and/or the second location, (n) a portion of the support structure may be curved away from the patient's nose along a longitudinal axis of the support structure in an undeformed state, and/or (o) the undercushion may be structured to only support the patient contacting surface against the patient's lip superior.

An aspect of the present technology is directed to a patient interface that comprises: a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; a decoupling structure; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered, and wherein vent structure further comprises openings through the decoupling structure and openings through the plenum chamber.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
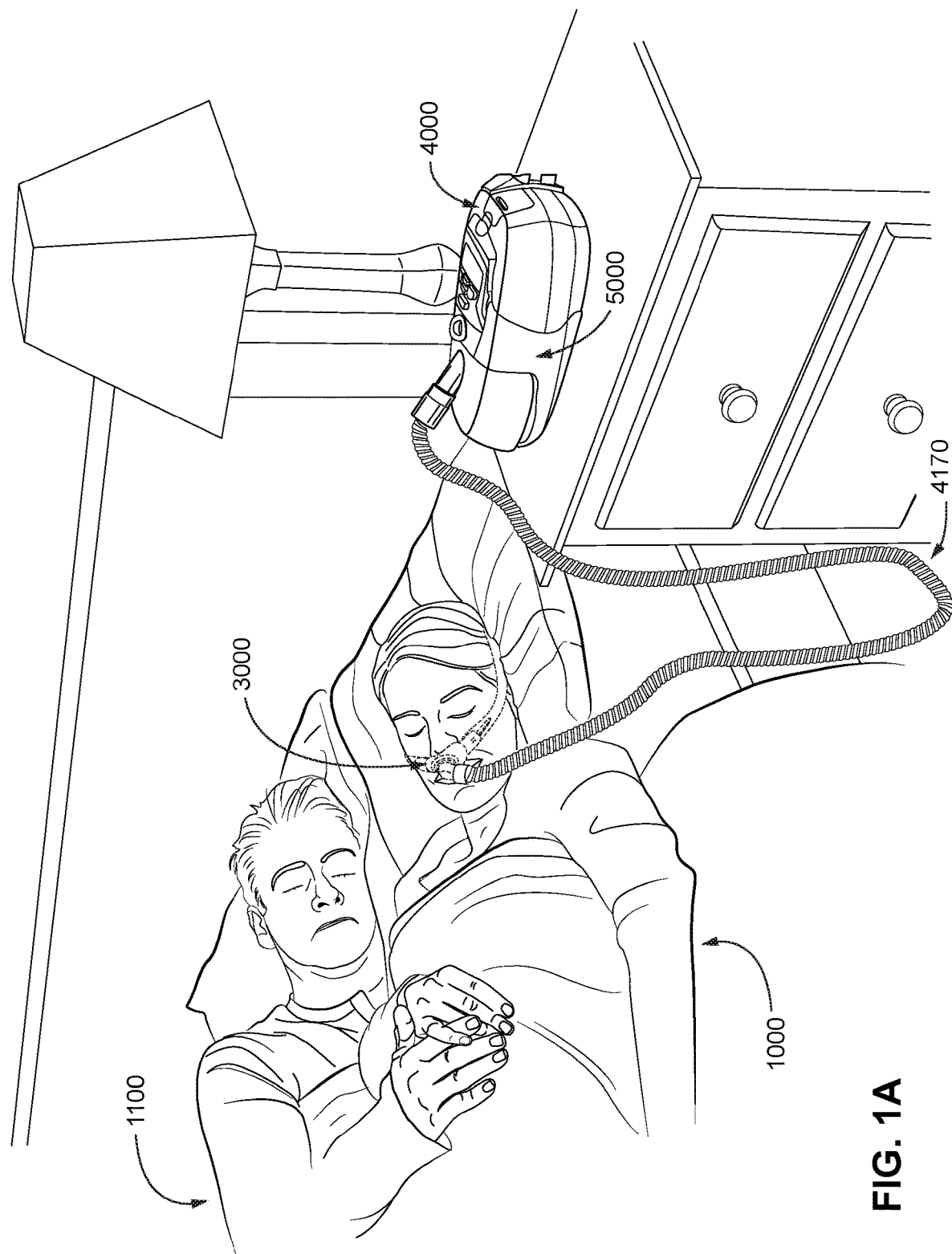
Figure 1B:
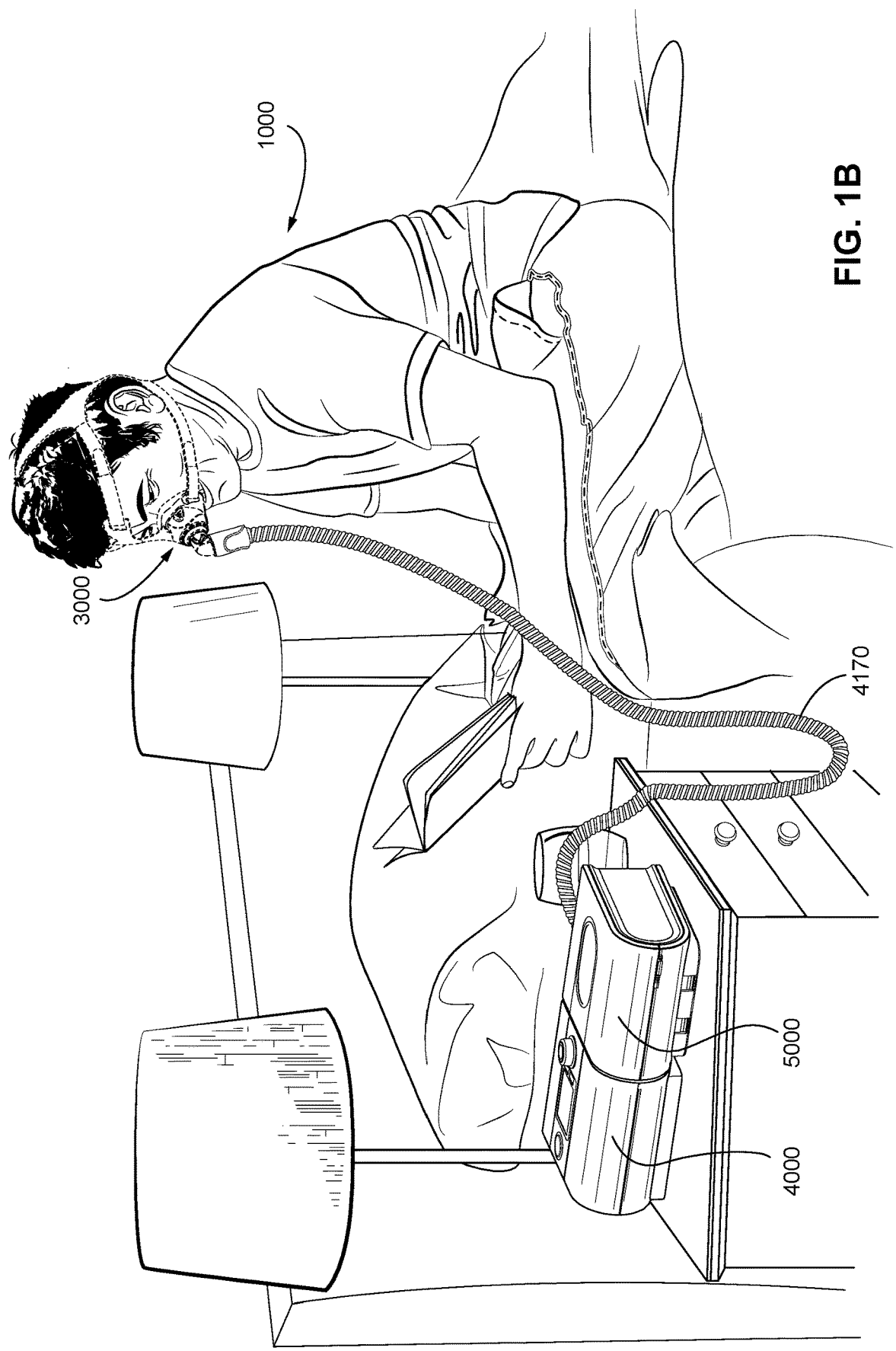
Figure 1C:
Figure 2A:
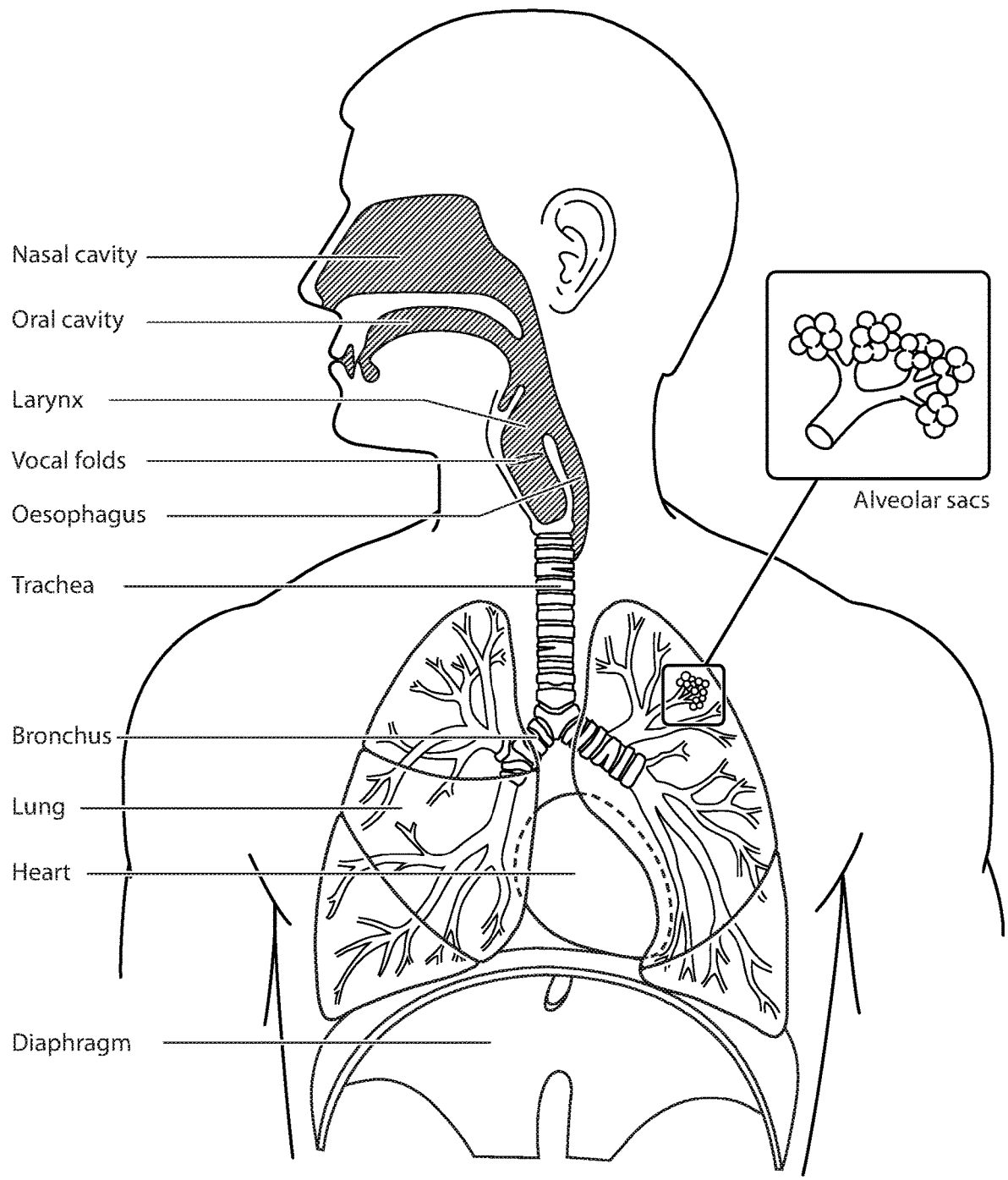
FIG. 2A shows an overview of a human respiratory system including the nasal and oral cavities, the larynx, vocal folds, oesophagus, trachea, bronchus, lung, alveolar sacs, heart and diaphragm.
Figure 2B:
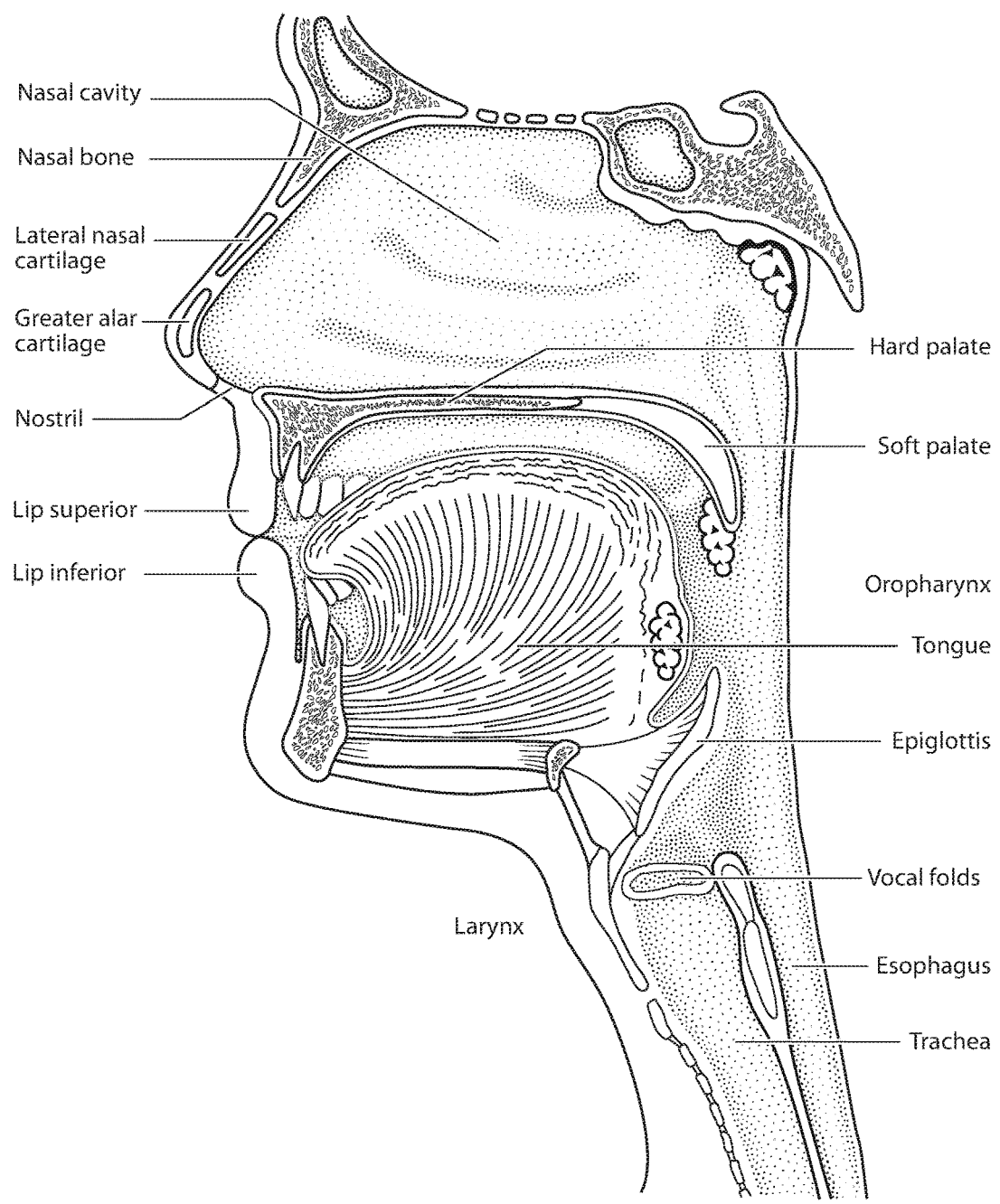
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
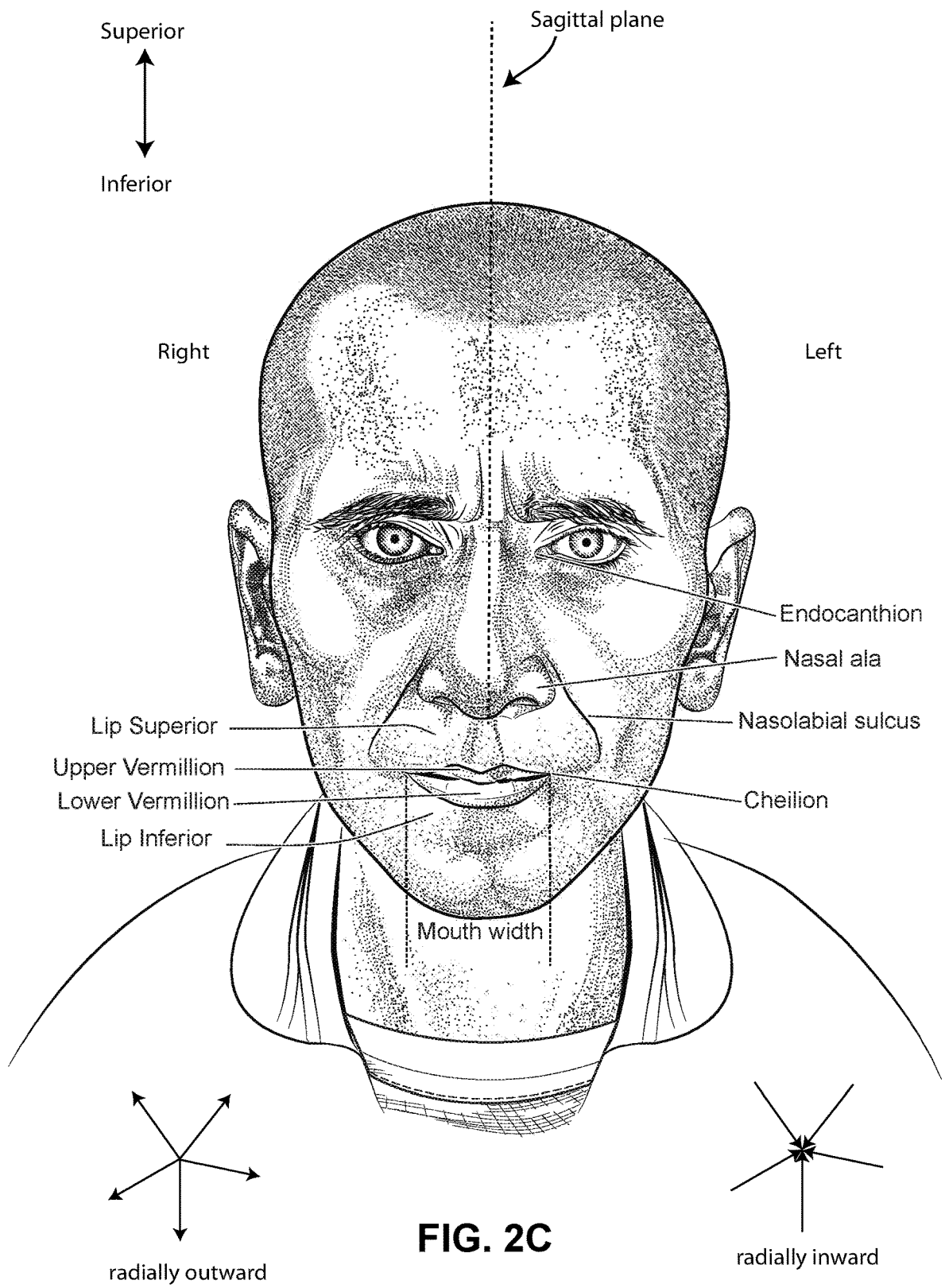
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
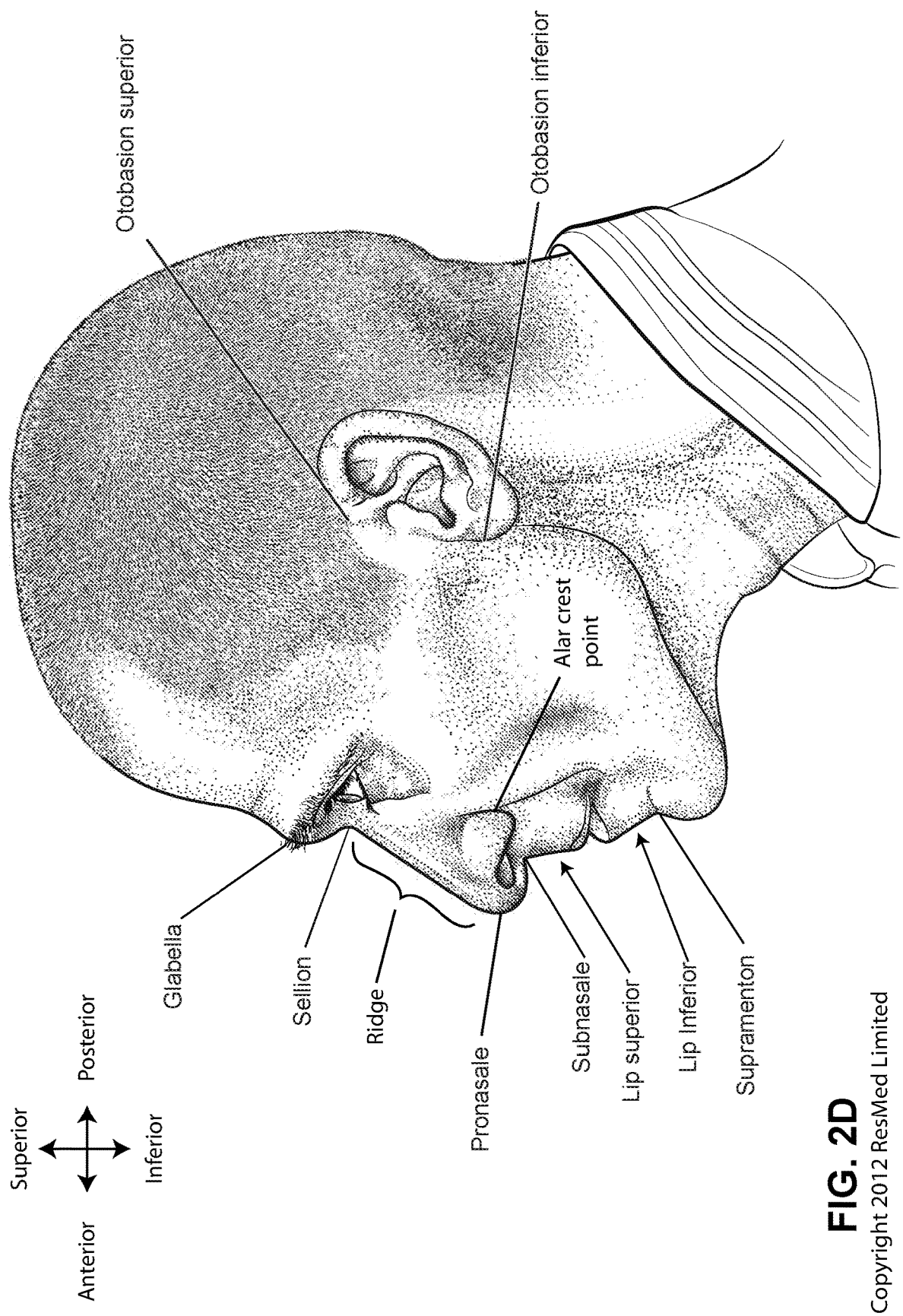
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
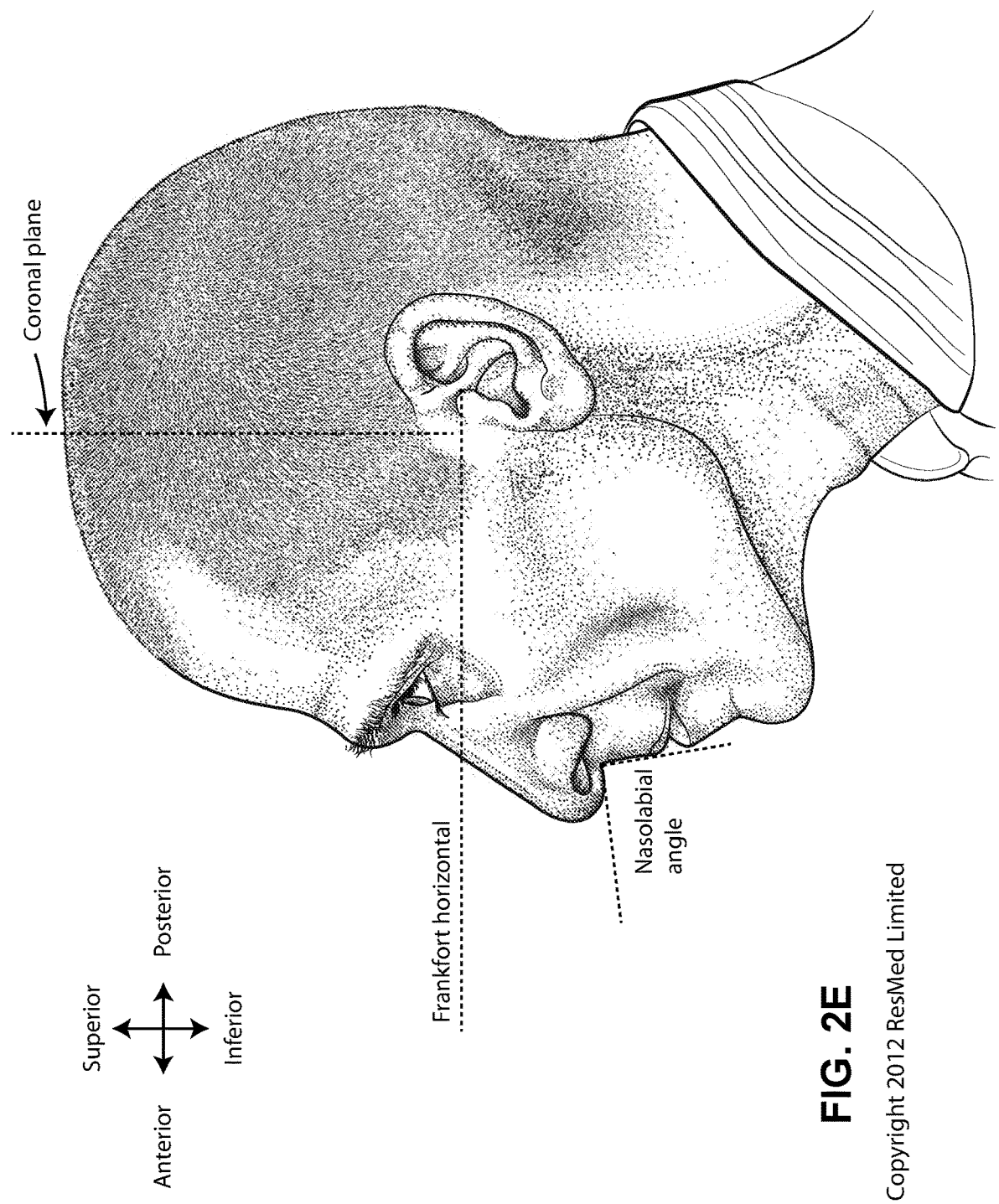

FIG. 2E is a further side view of a head. The approximate locations of the Frankfort horizontal and nasolabial angle are indicated. The coronal plane is also indicated.

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
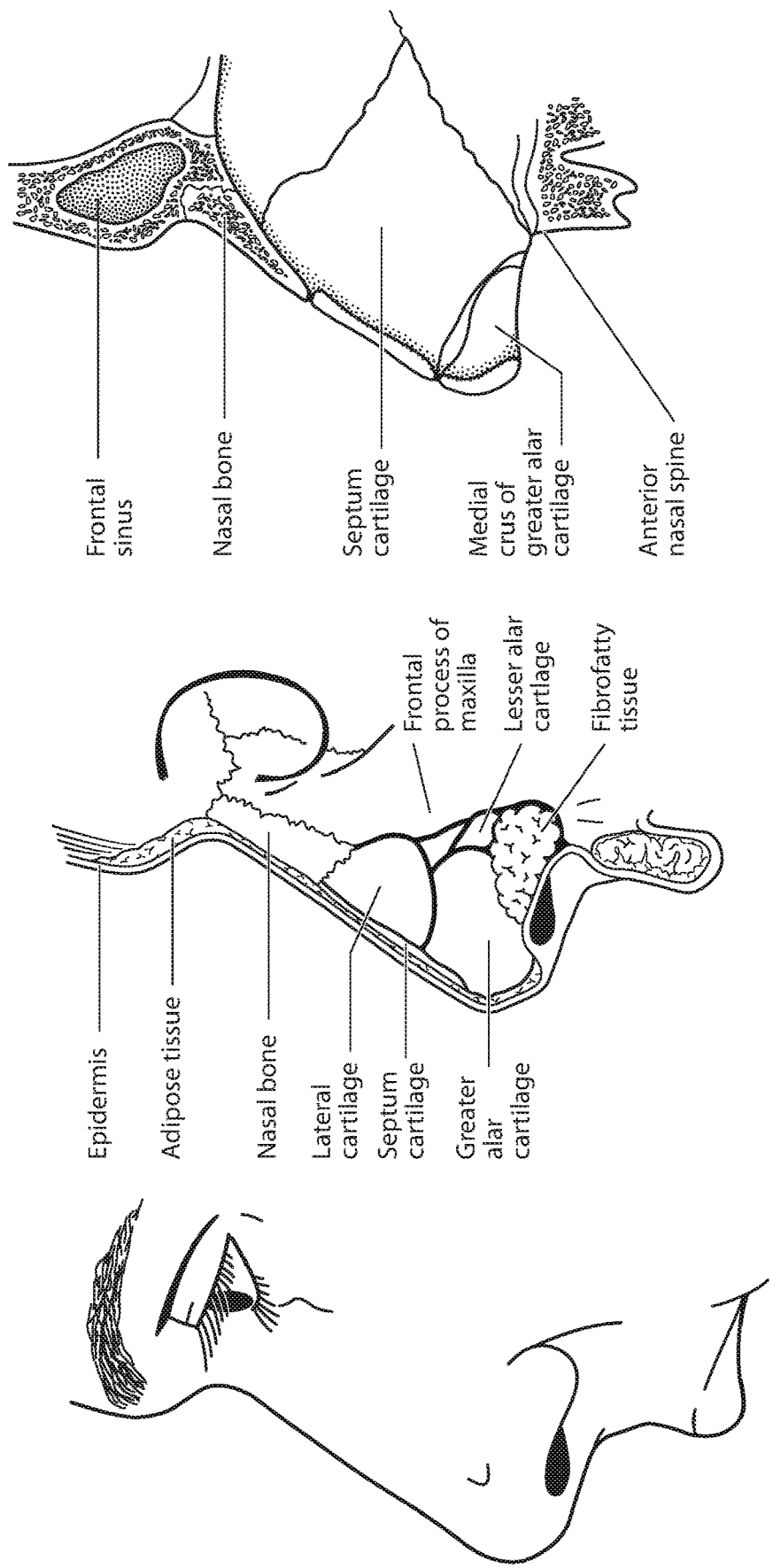

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
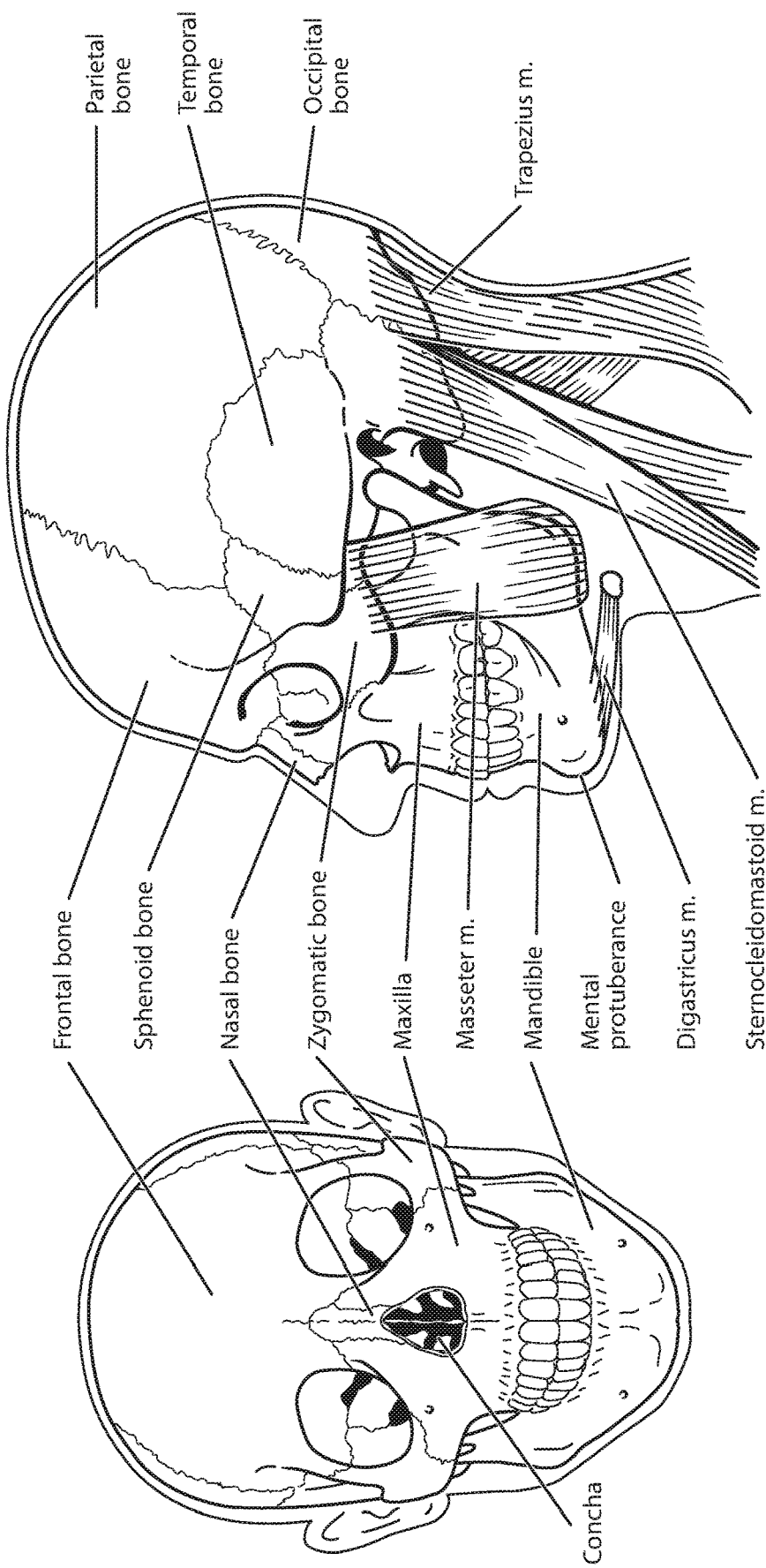

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
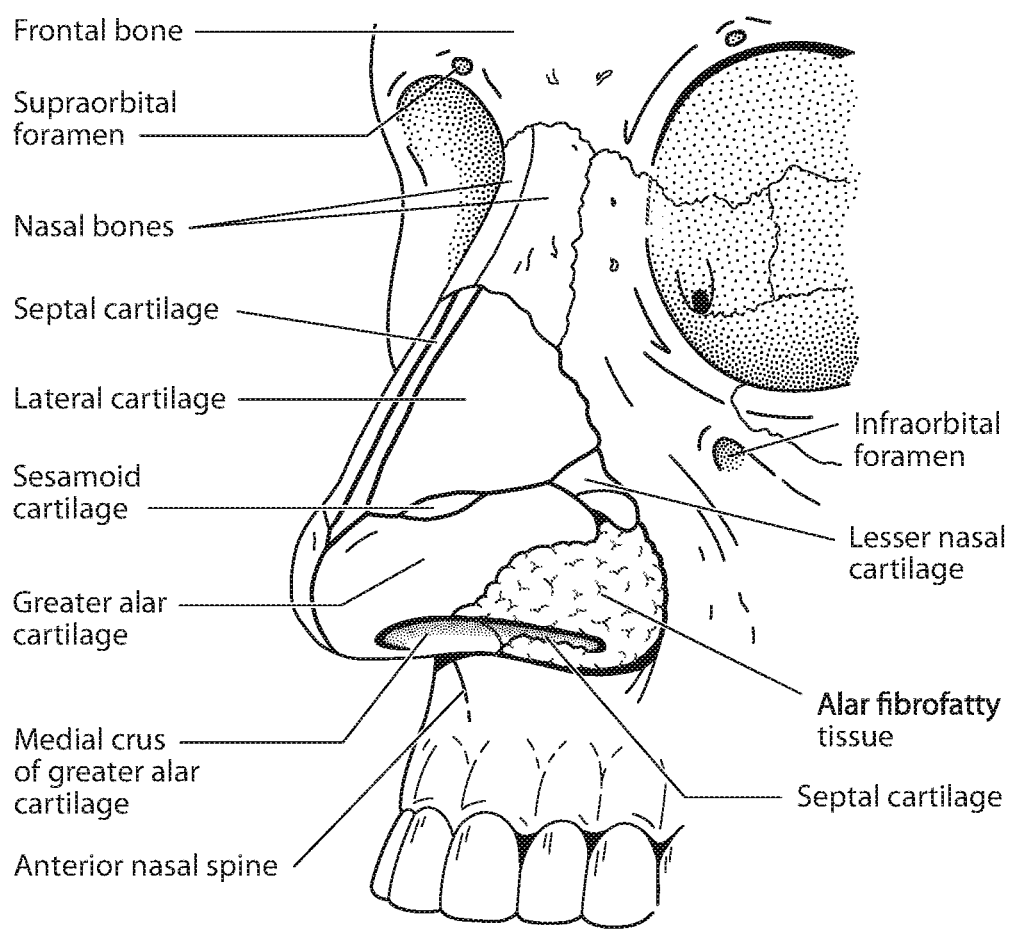

FIG. 2L shows an anterolateral view of a nose.

4.3 Patient Interface

Figure 3A:
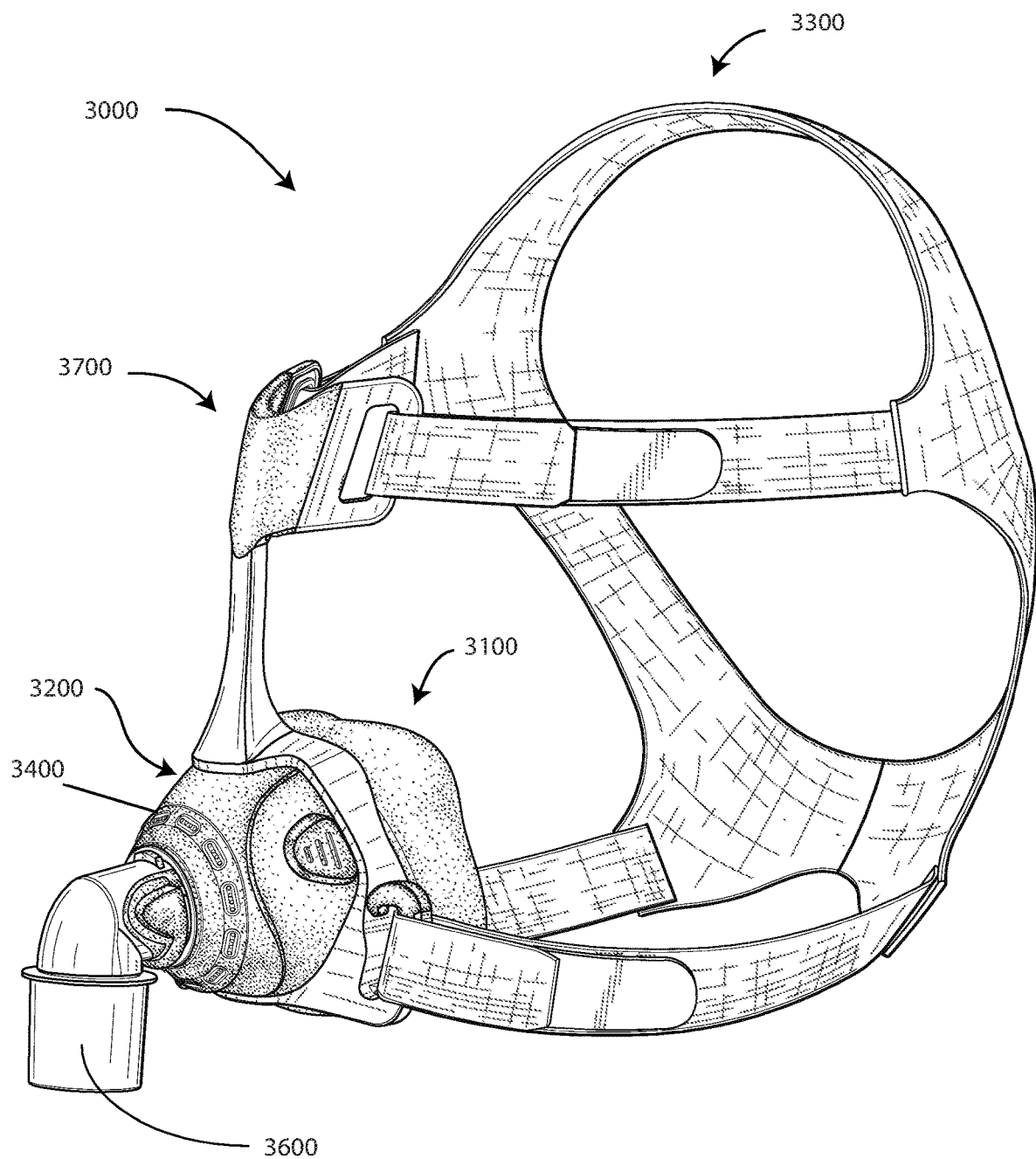

FIG. 3A shows a patient interface in the form of a nasal mask in accordance with one form of the present technology.

Figure 3B:
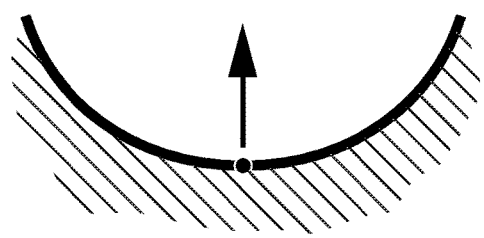

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
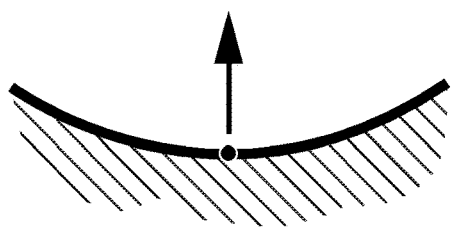

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
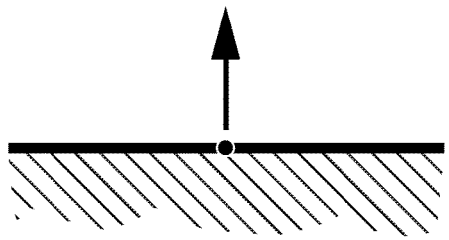

FIG. 3D shows a schematic of a cross-section through a structure at a point. An outward normal at the point is indicated. The curvature at the point has a value of zero.

Figure 3E:
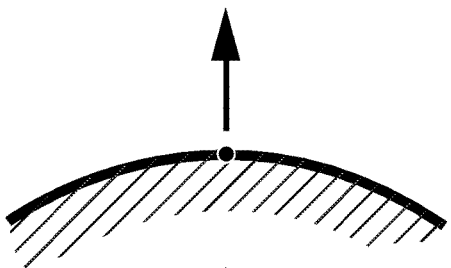

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
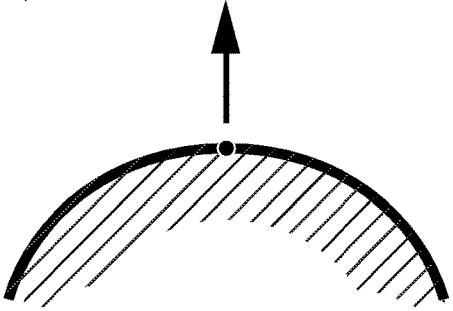

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
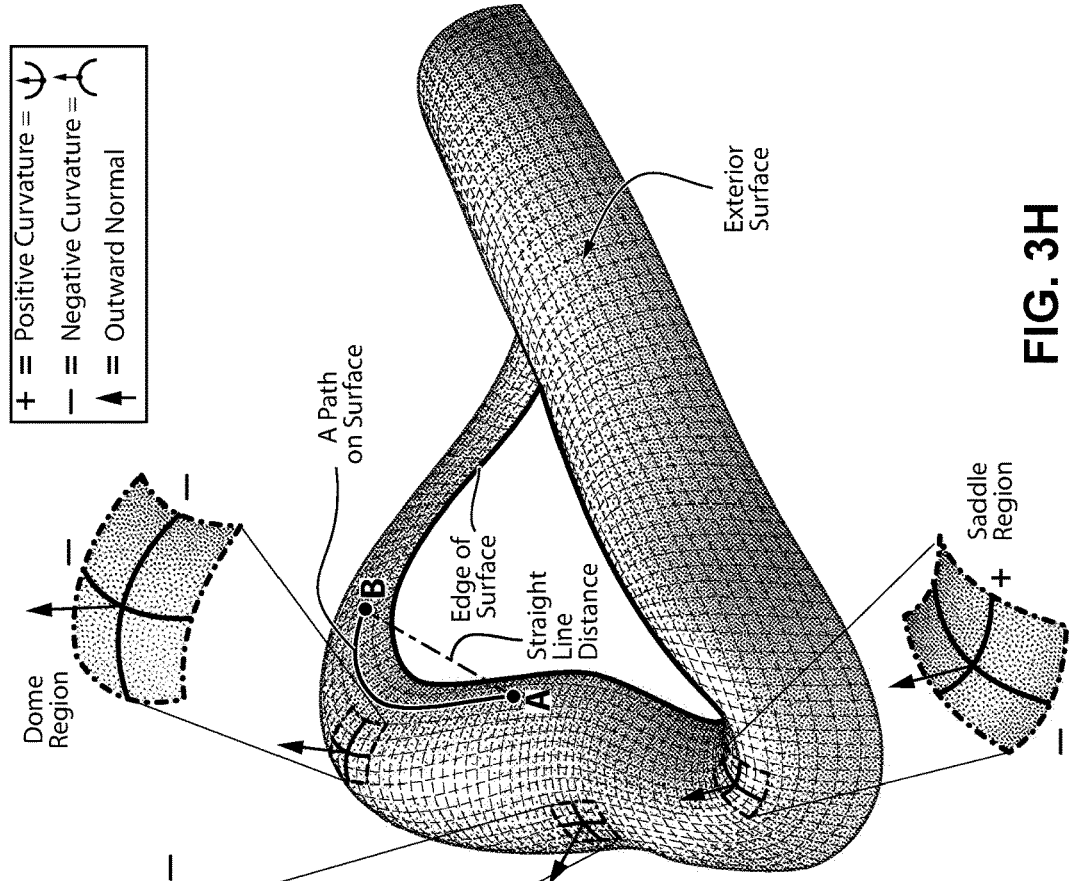
Figure 3G:
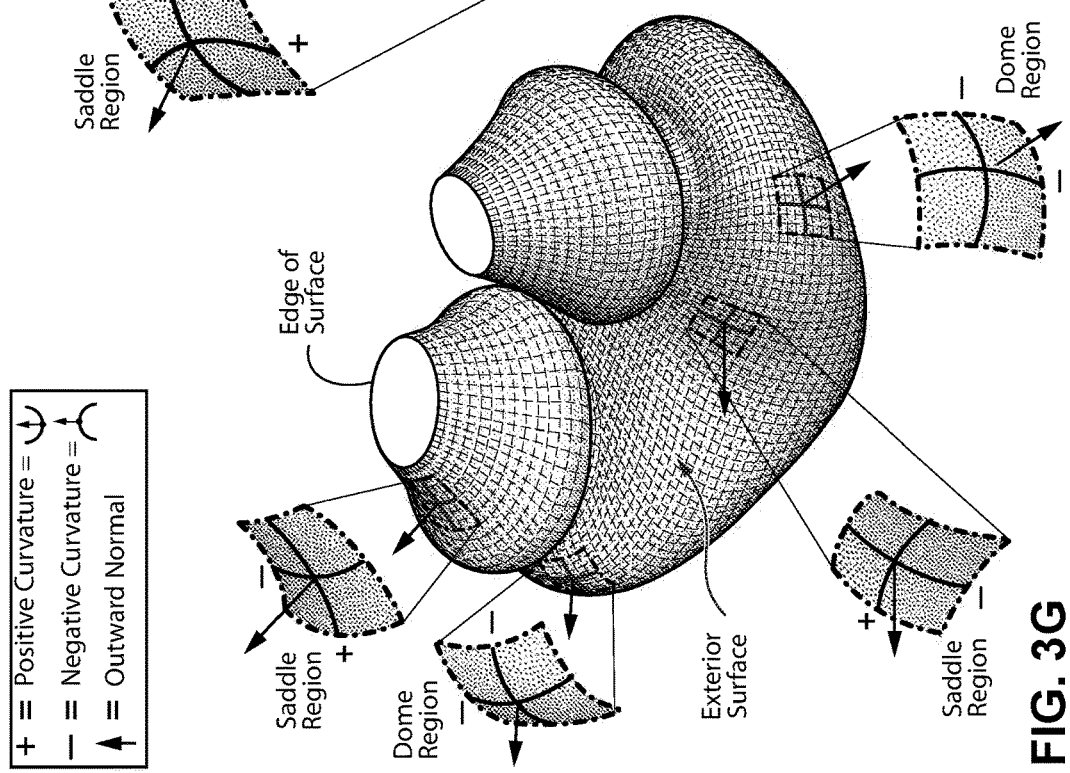

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
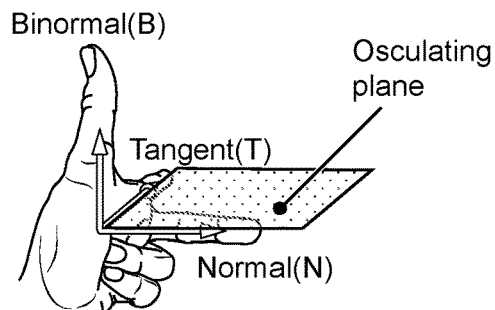

FIG. 3O illustrates a left-hand rule.

Figure 3P:
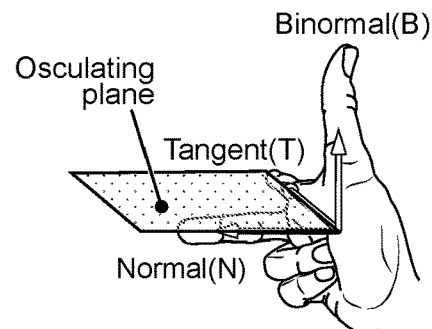

FIG. 3P illustrates a right-hand rule.

Figure 3Q:
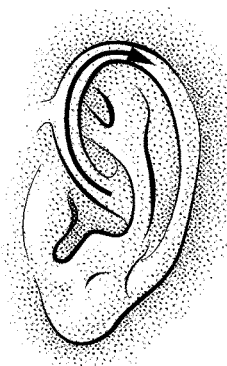

FIG. 3Q shows a left ear, including the left ear helix.

Figure 3S:
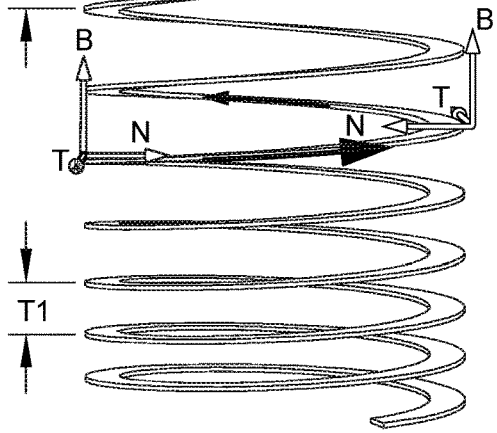
Figure 3R:
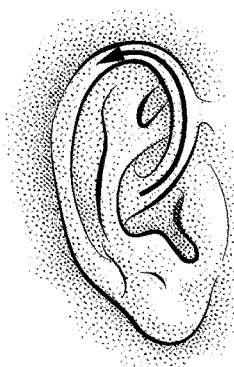

FIG. 3R shows a right ear, including the right ear helix.

FIG. 3S shows a right-hand helix.

Figure 3T:
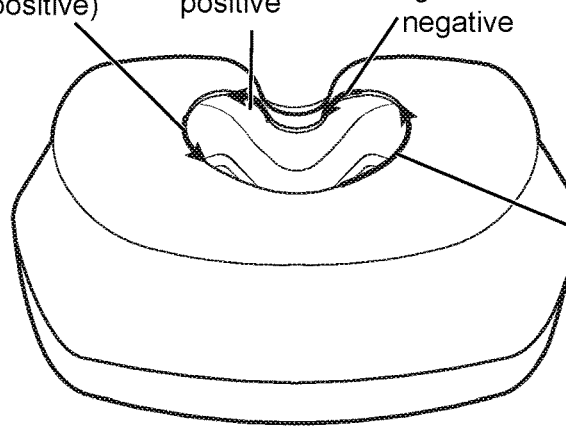

FIG. 3T shows a view of a mask, including the sign of the torsion of the space curve defined by the edge of the sealing membrane in different regions of the mask.

Figure 3U:
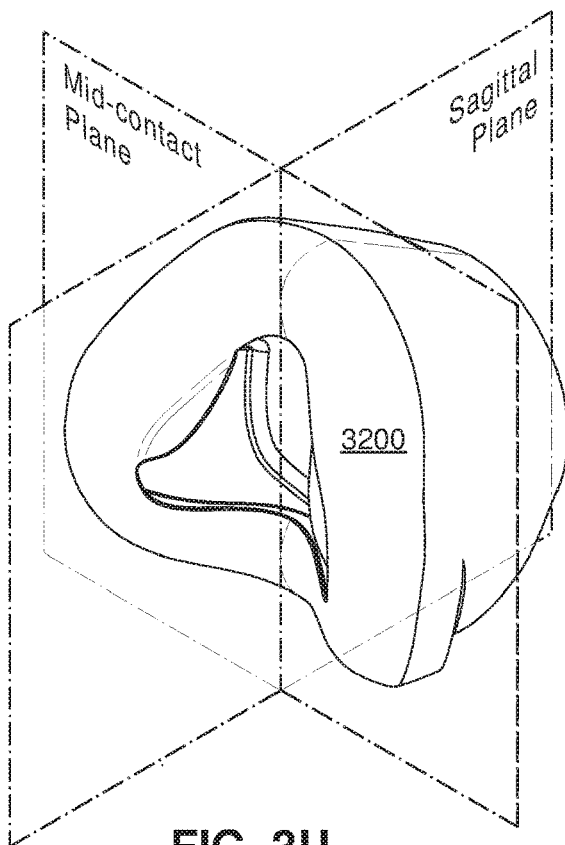

FIG. 3U shows a view of a plenum chamber (cushion assembly) 3200 showing a sagittal plane and a mid-contact plane.

Figure 3V:
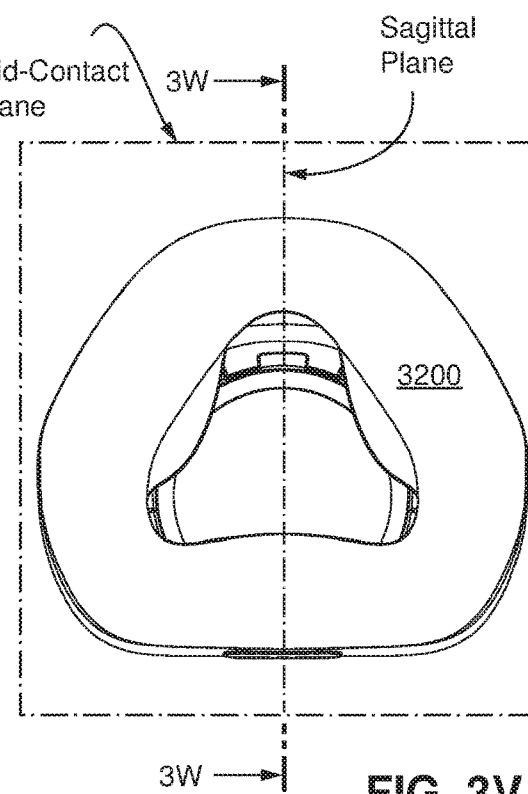

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
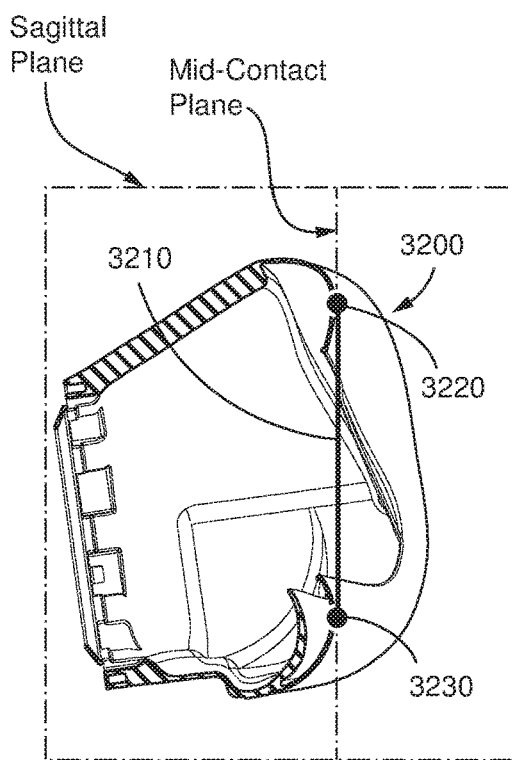

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
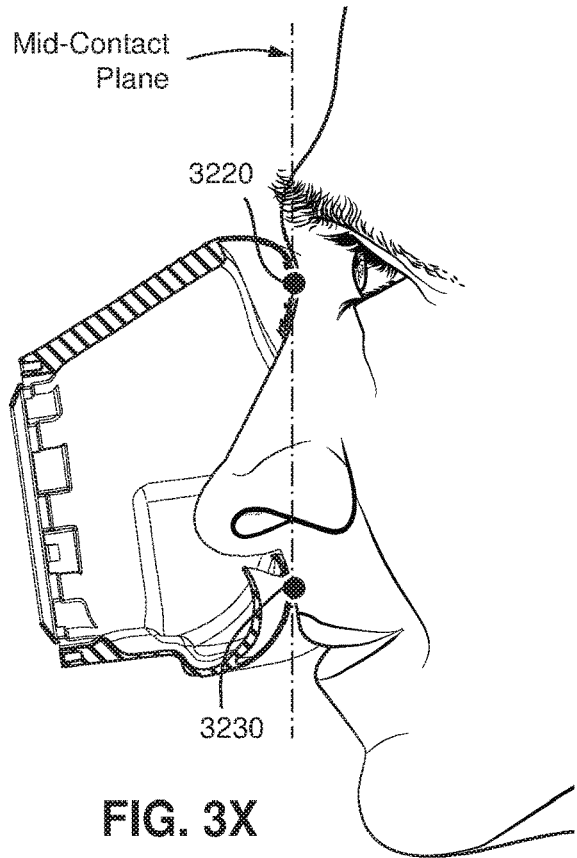

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
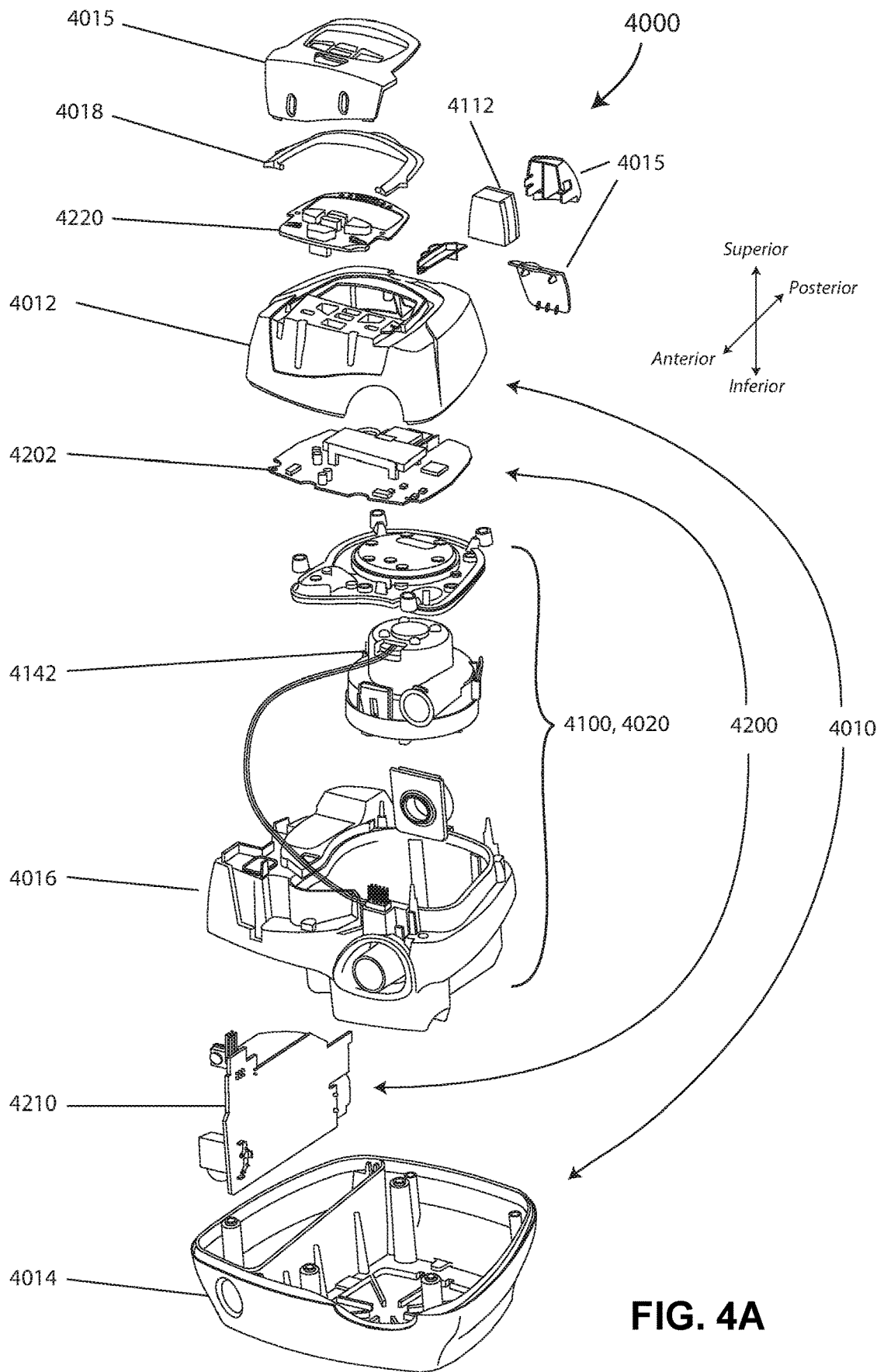

FIG. 4A shows an RPT device in accordance with one form of the present technology.

Figure 4B:
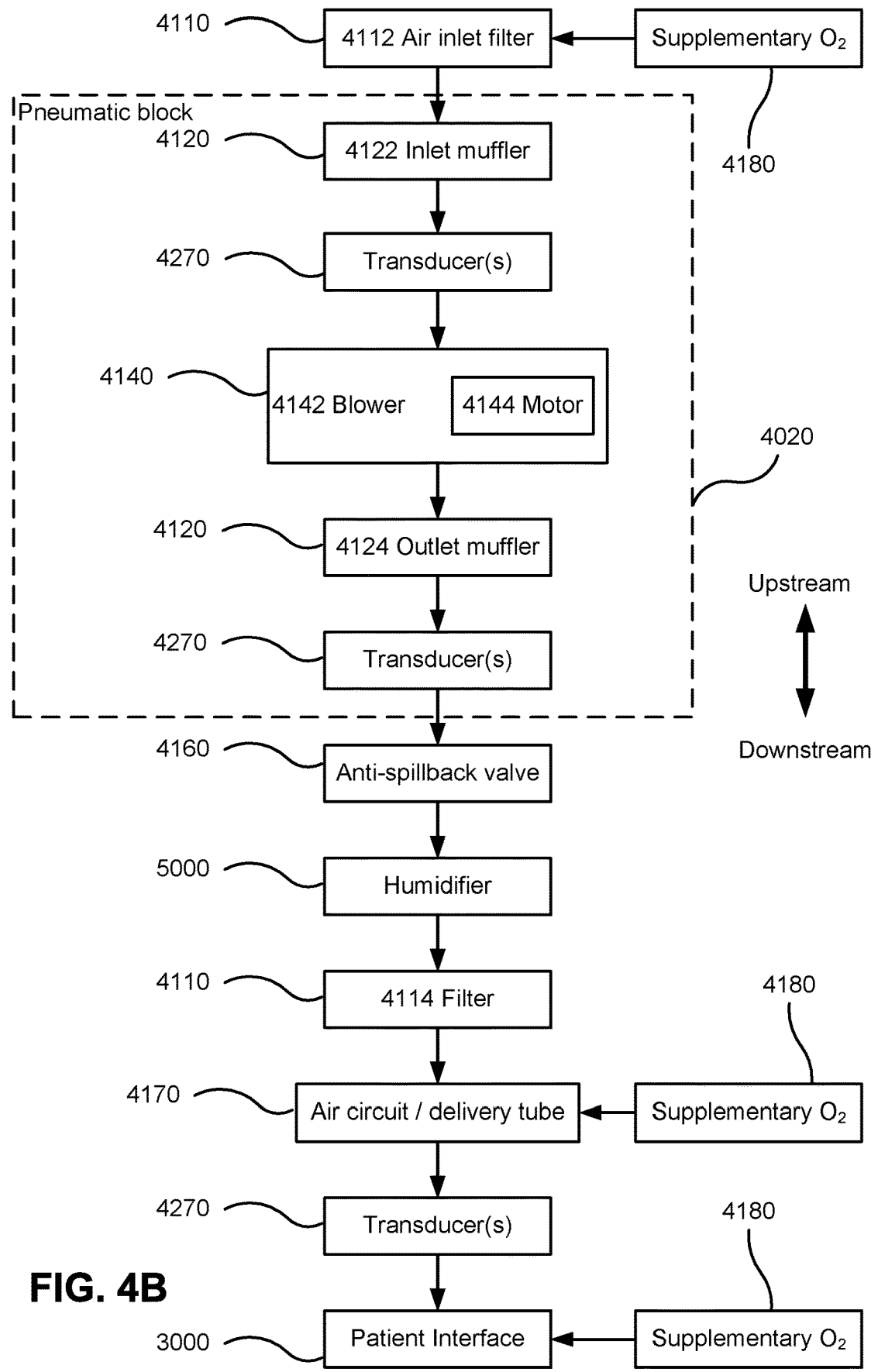

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
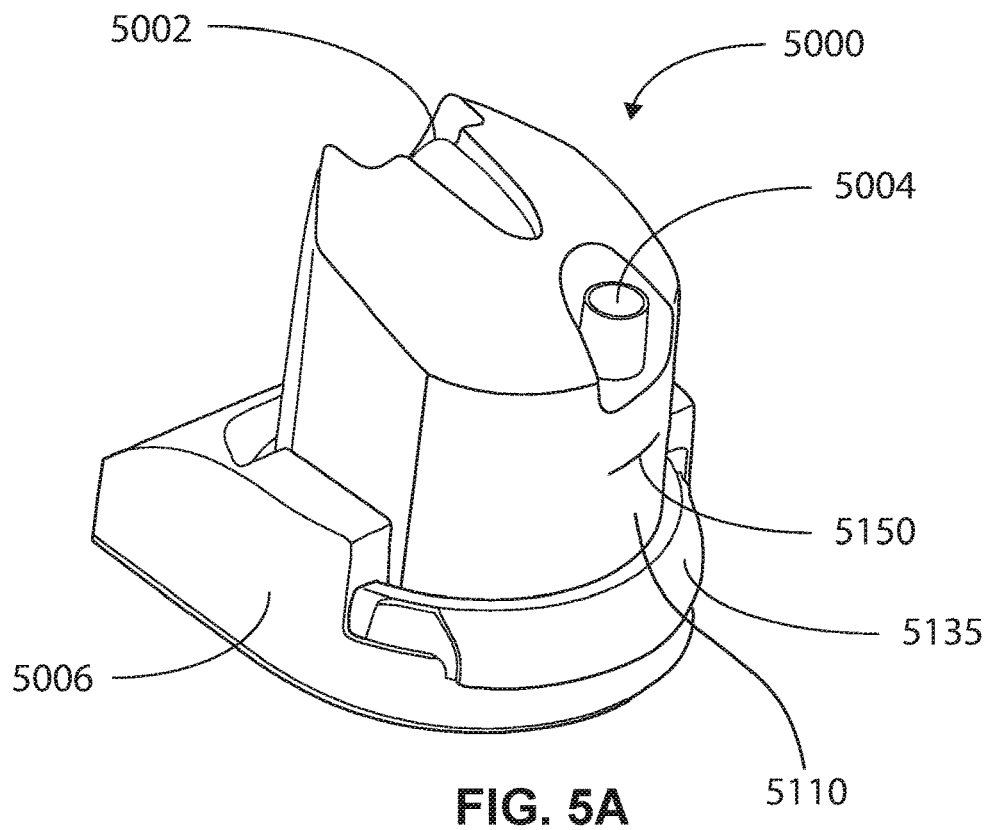

FIG. 5A shows an isometric view of a humidifier in accordance with one form of the present technology.

Figure 5B:
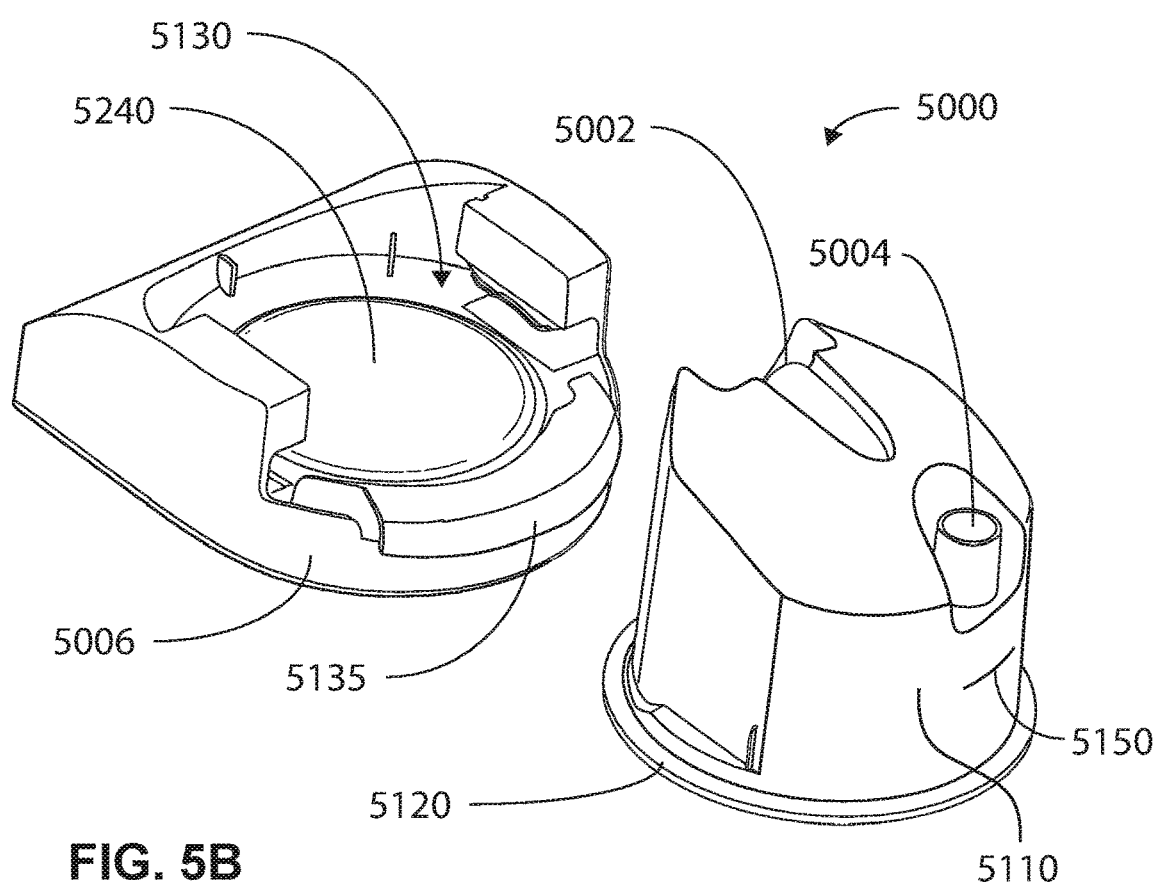

FIG. 5B shows an isometric view of a humidifier in accordance with one form of the present technology, showing a humidifier reservoir 5110 removed from the humidifier reservoir dock 5130.

4.6 Breathing Waveforms

Figure 6:
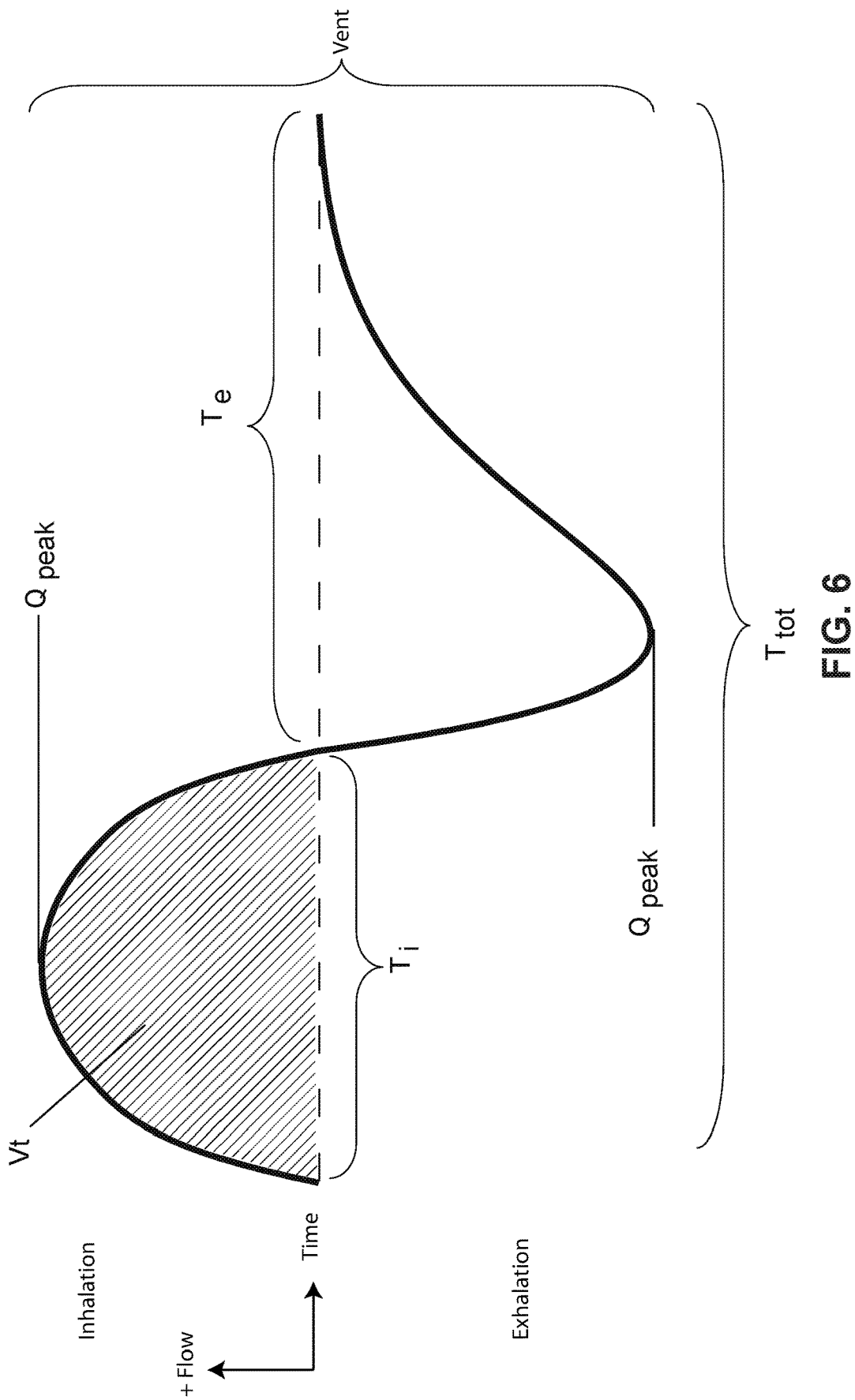

FIG. 6 shows a model typical breath waveform of a person while sleeping.

4.7 Patient Interface According to the Present Technology

Figure 7A:
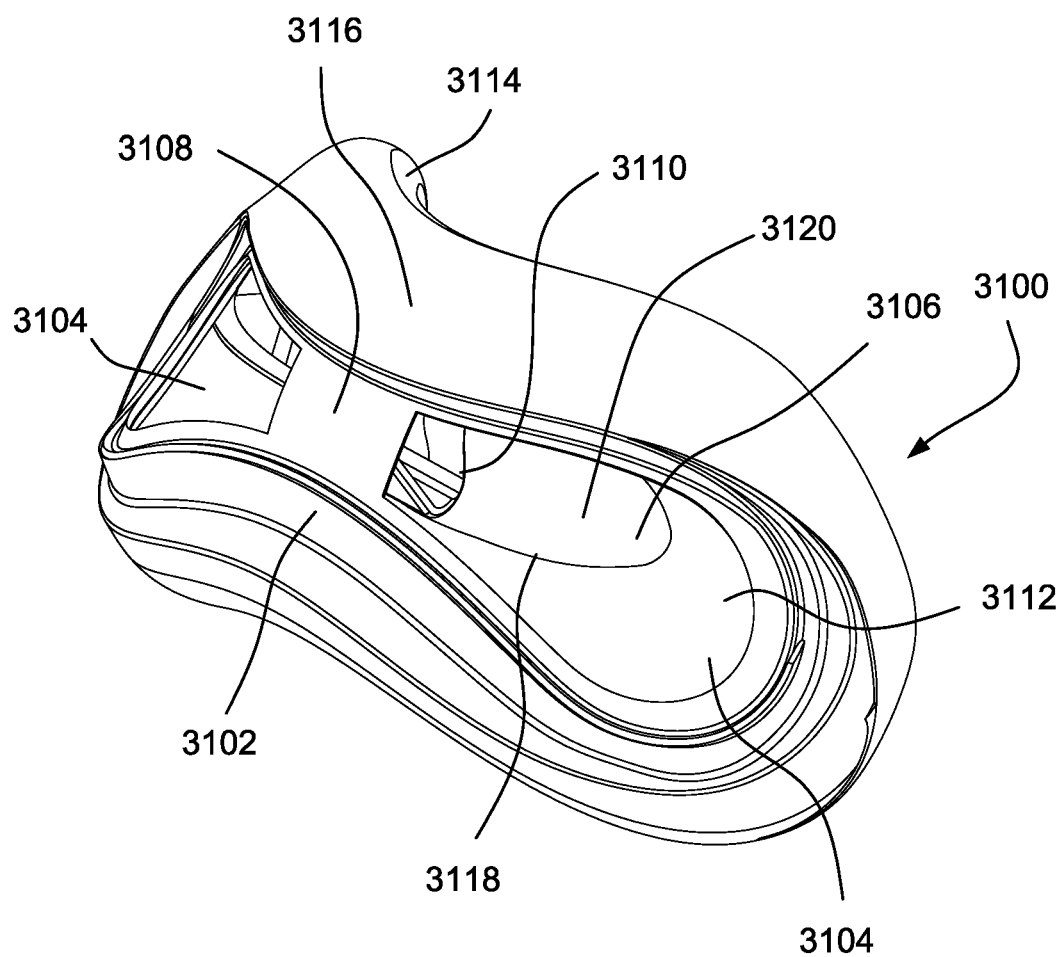

FIG. 7A depicts an anterior perspective view of a seal-forming structure of a patient interface according to an example of the present technology.

Figure 7B:
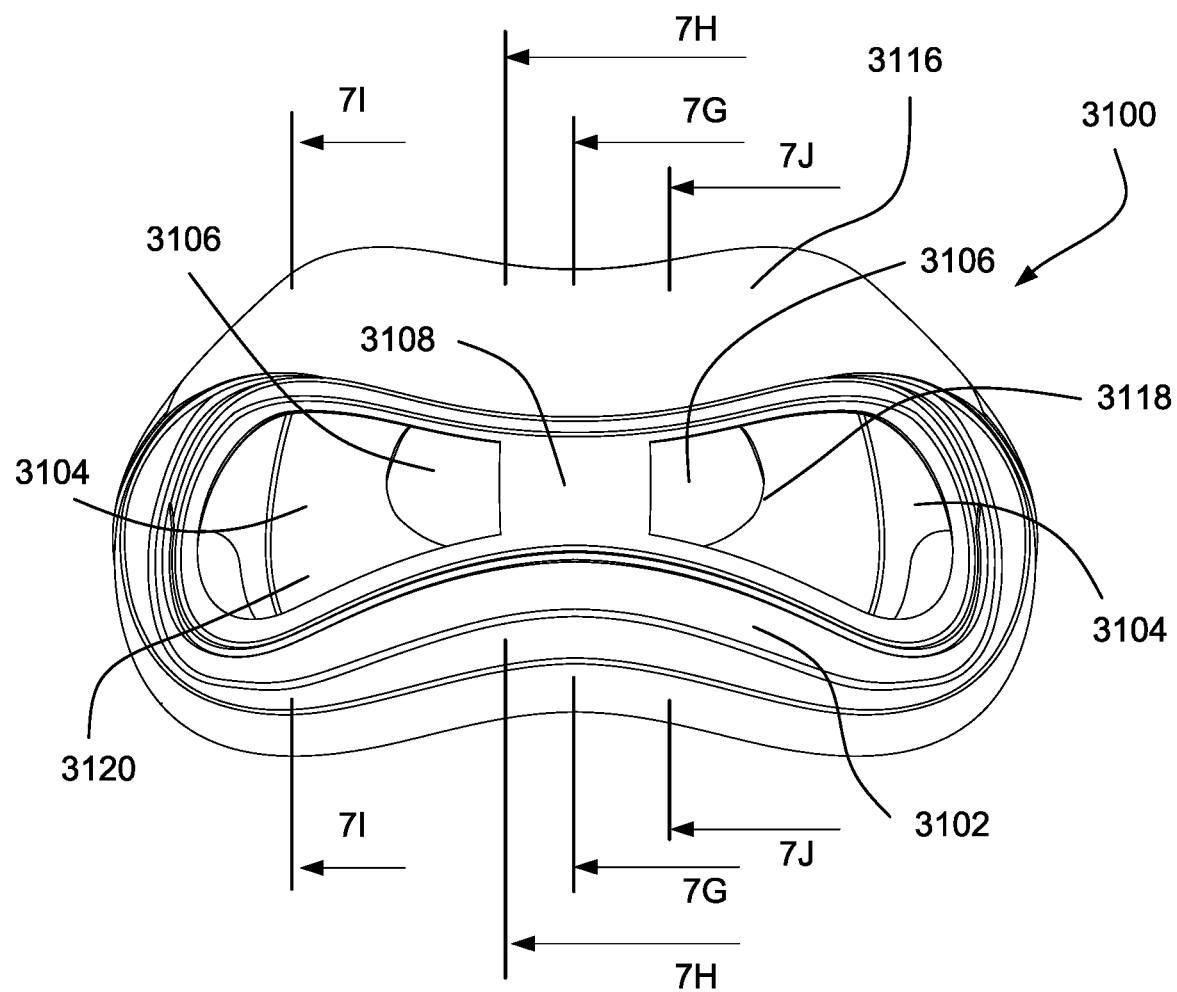

FIG. 7B depicts an anterior view of a seal-forming structure of a patient interface according to an example of the present technology.

Figure 7C:
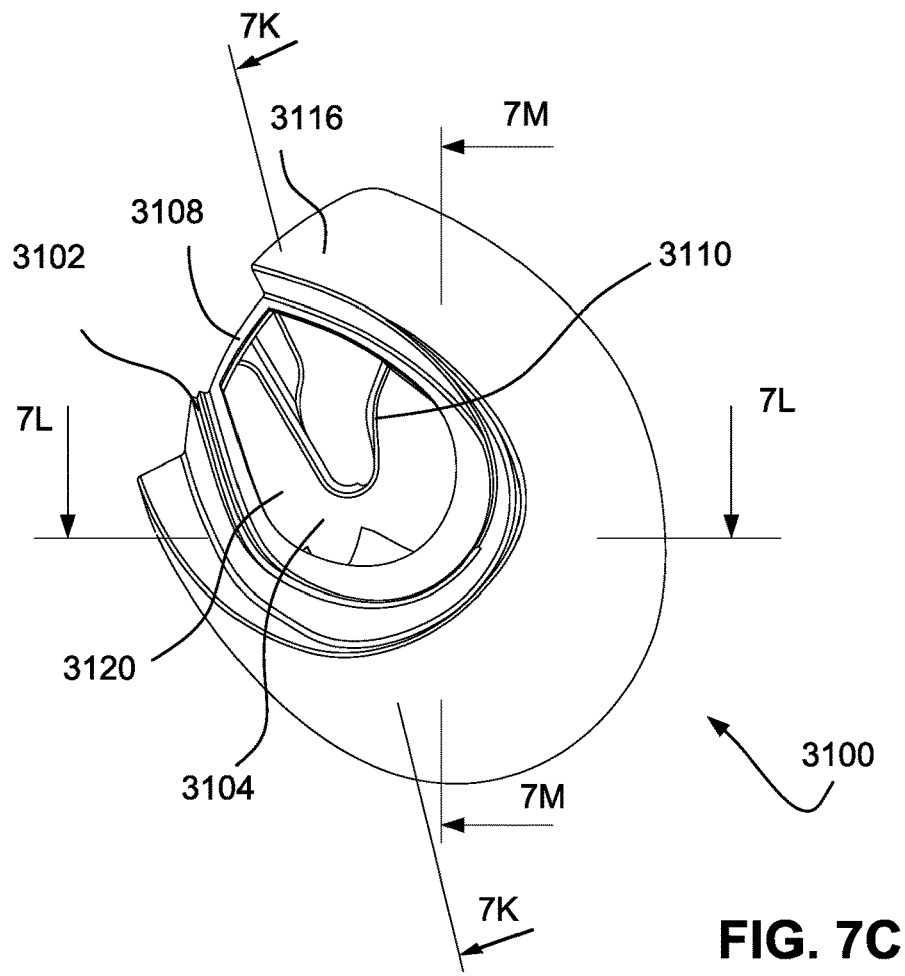

FIG. 7C depicts a lateral view of a seal-forming structure of a patient interface according to an example of the present technology.

Figure 7D:
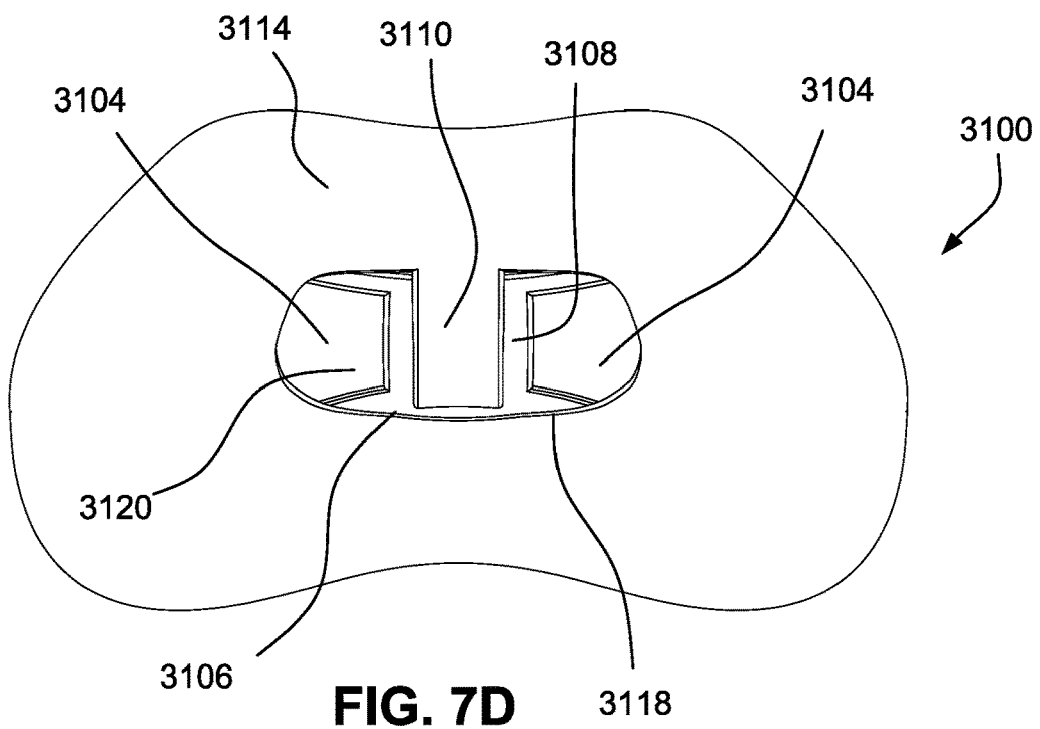

FIG. 7D depicts a posterior view of a seal-forming structure of a patient interface according to an example of the present technology.

Figure 7E:
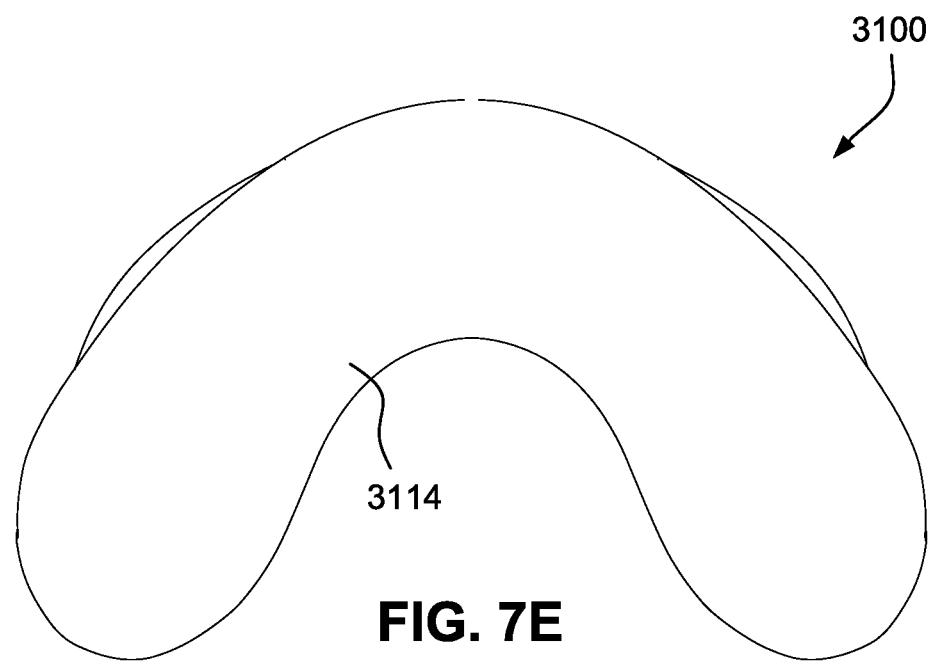

FIG. 7E depicts an inferior view of a seal-forming structure of a patient interface according to an example of the present technology.

Figure 7F:
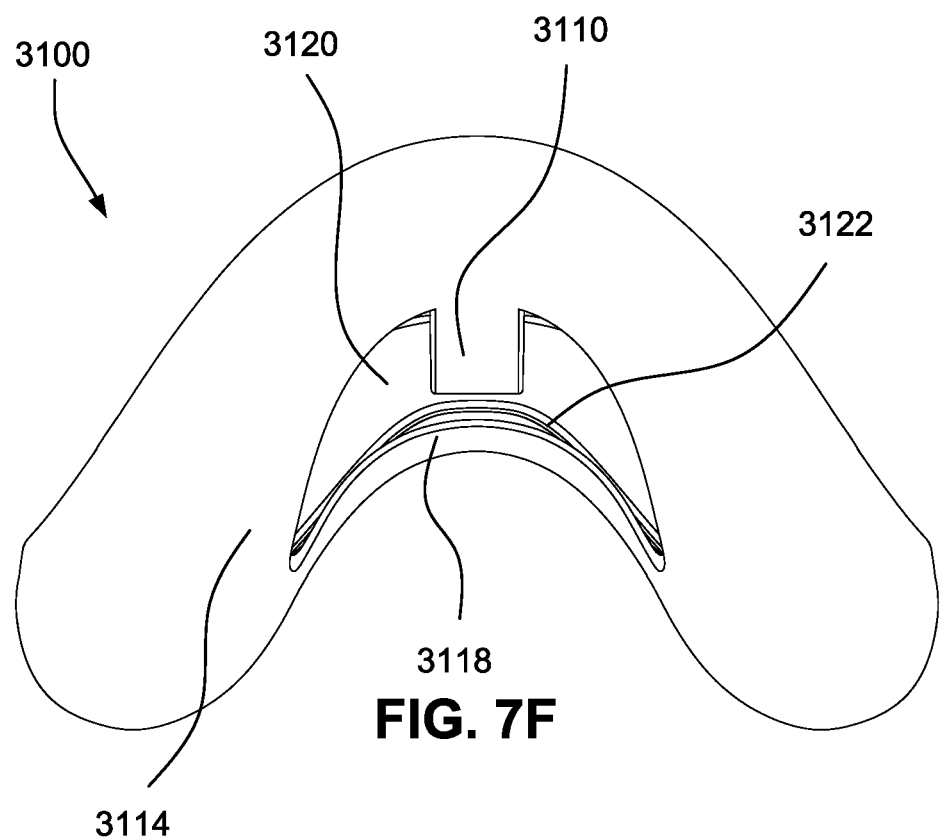

FIG. 7F depicts a superior view of a seal-forming structure of a patient interface according to an example of the present technology.

Figure 7G:
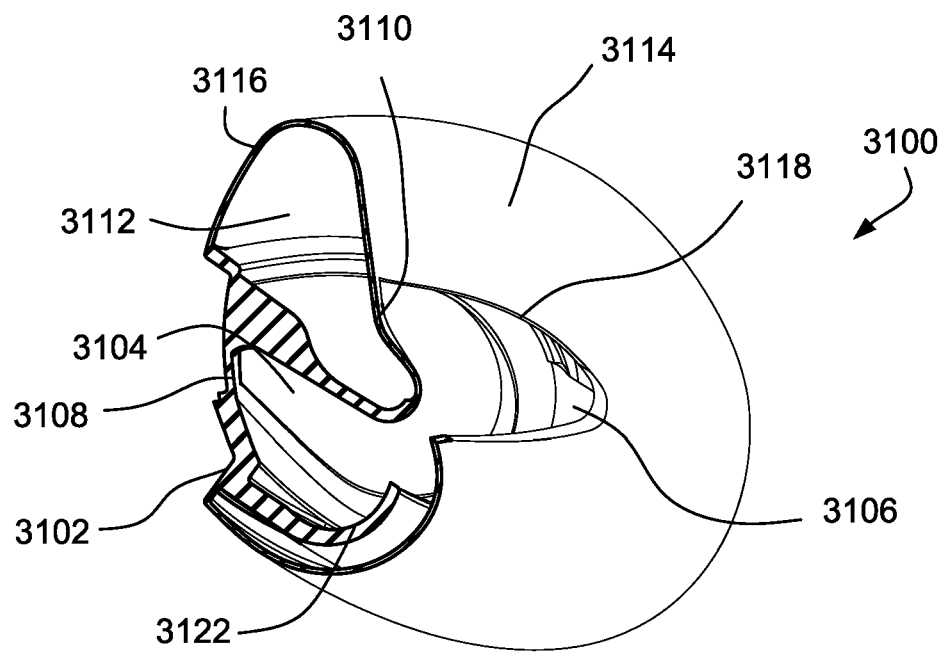

FIG. 7G depicts a cross-sectional view of a seal-forming structure of a patient interface taken through line 7G-7G of FIG. 7B according to an example of the present technology.

Figure 7H:
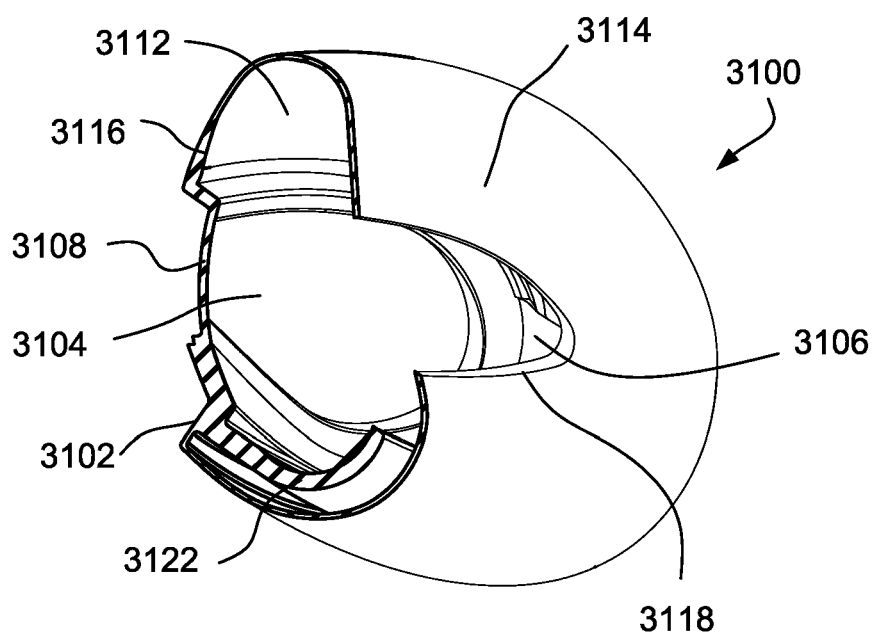

FIG. 7H depicts a cross-sectional view of a seal-forming structure of a patient interface taken through line 7H-7H of FIG. 7B according to an example of the present technology.

Figure 7I:
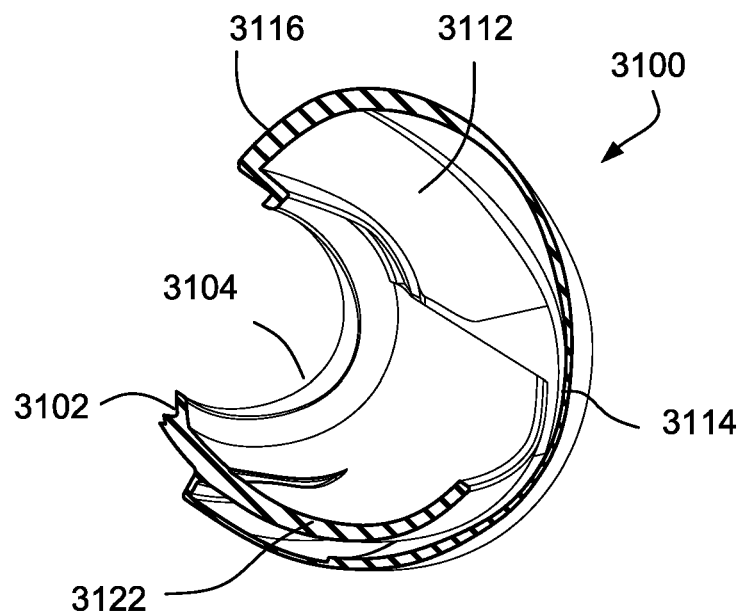

FIG. 7I depicts a cross-sectional view of a seal-forming structure of a patient interface taken through line 7I-7I of FIG. 7B according to an example of the present technology.

Figure 7J:
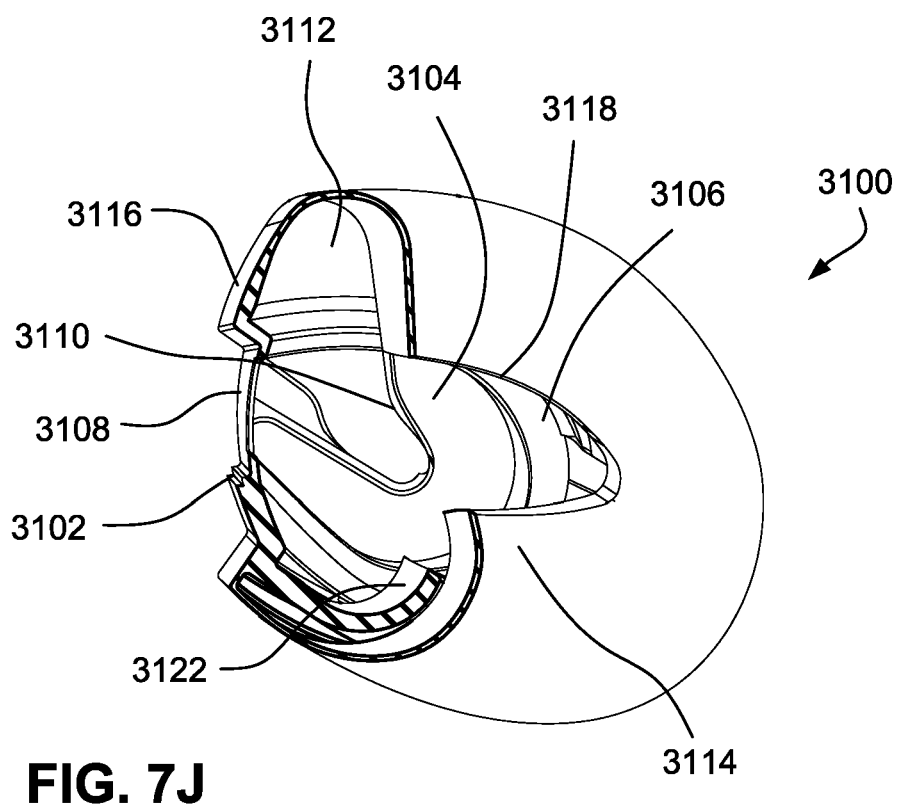

FIG. 7J depicts a cross-sectional view of a seal-forming structure of a patient interface taken through line 7J-7J of FIG. 7B according to an example of the present technology.

Figure 7K:
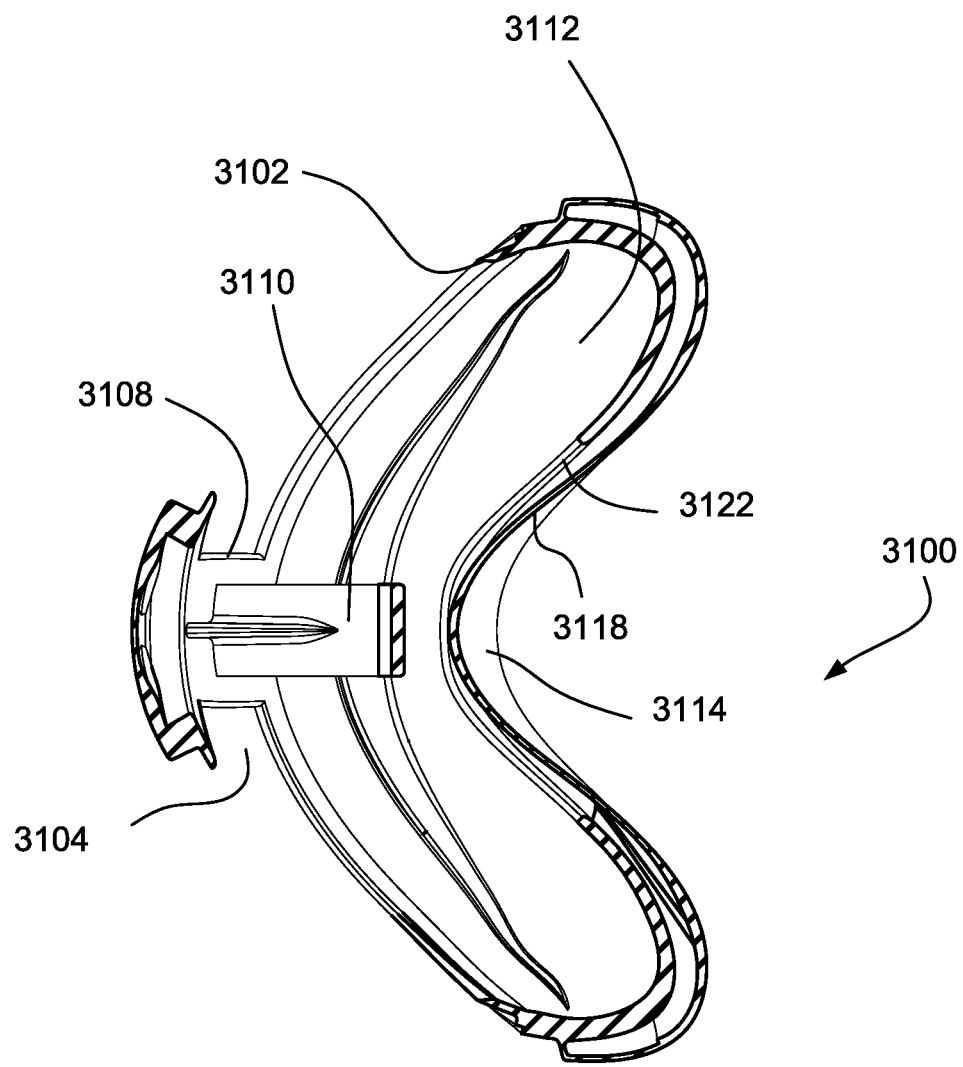

FIG. 7K depicts a cross-sectional view of a seal-forming structure of a patient interface taken through line 7K-7K of FIG. 7C according to an example of the present technology.

Figure 7L:
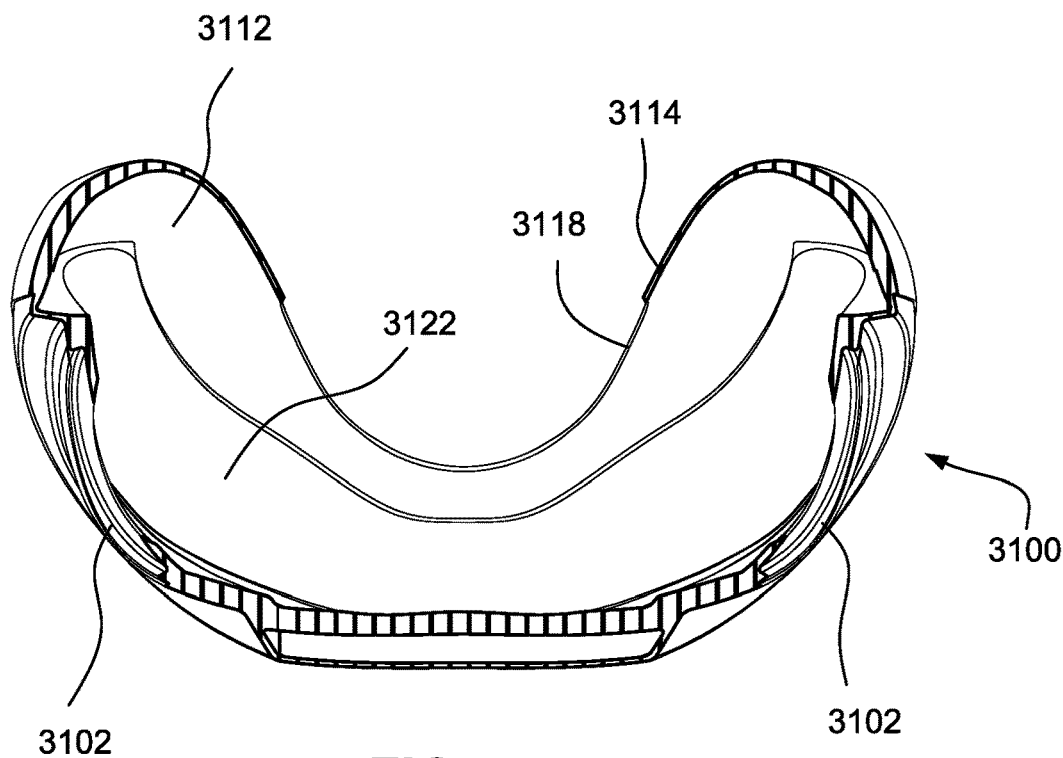

FIG. 7L depicts a cross-sectional view of a seal-forming structure of a patient interface taken through line 7L-7L of FIG. 7C according to an example of the present technology.

Figure 7M:
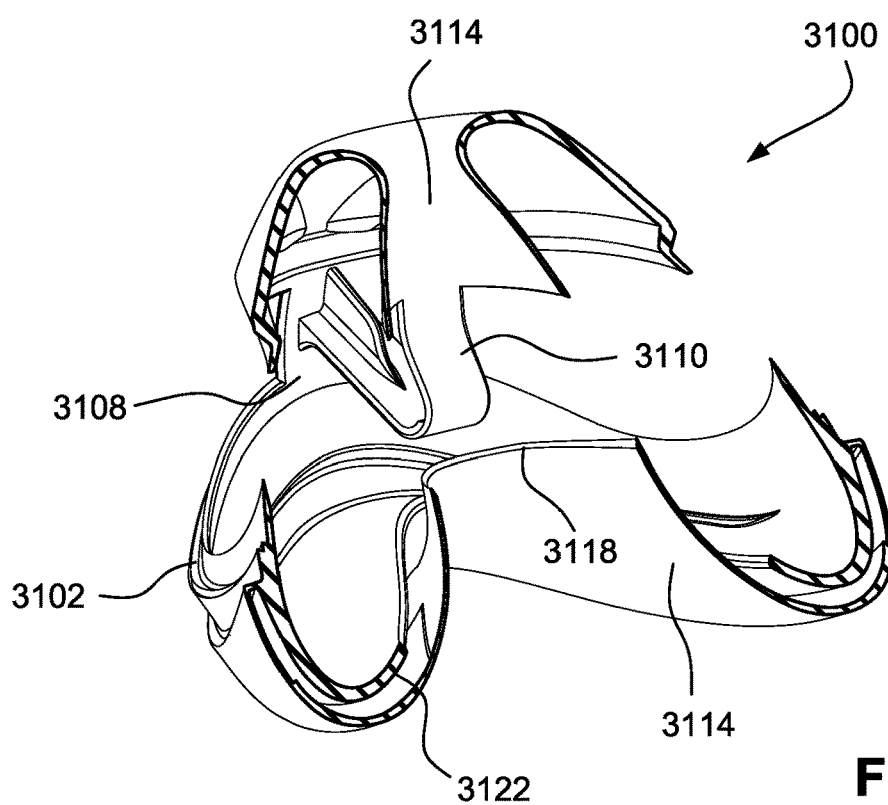

FIG. 7M depicts a cross-sectional view of a seal-forming structure of a patient interface taken through line 7M-7M of FIG. 7C according to an example of the present technology.

FIG. 8A depicts a posterior perspective view of a decoupling structure of a patient interface according to an example of the present technology.

FIG. 8B depicts an anterior perspective view of a decoupling structure of a patient interface according to an example of the present technology.

FIG. 9A depicts a posterior perspective view of a decoupling structure of a patient interface according to an example of the present technology.

FIG. 9B depicts an anterior perspective view of a decoupling structure of a patient interface according to an example of the present technology.

Figure 10:
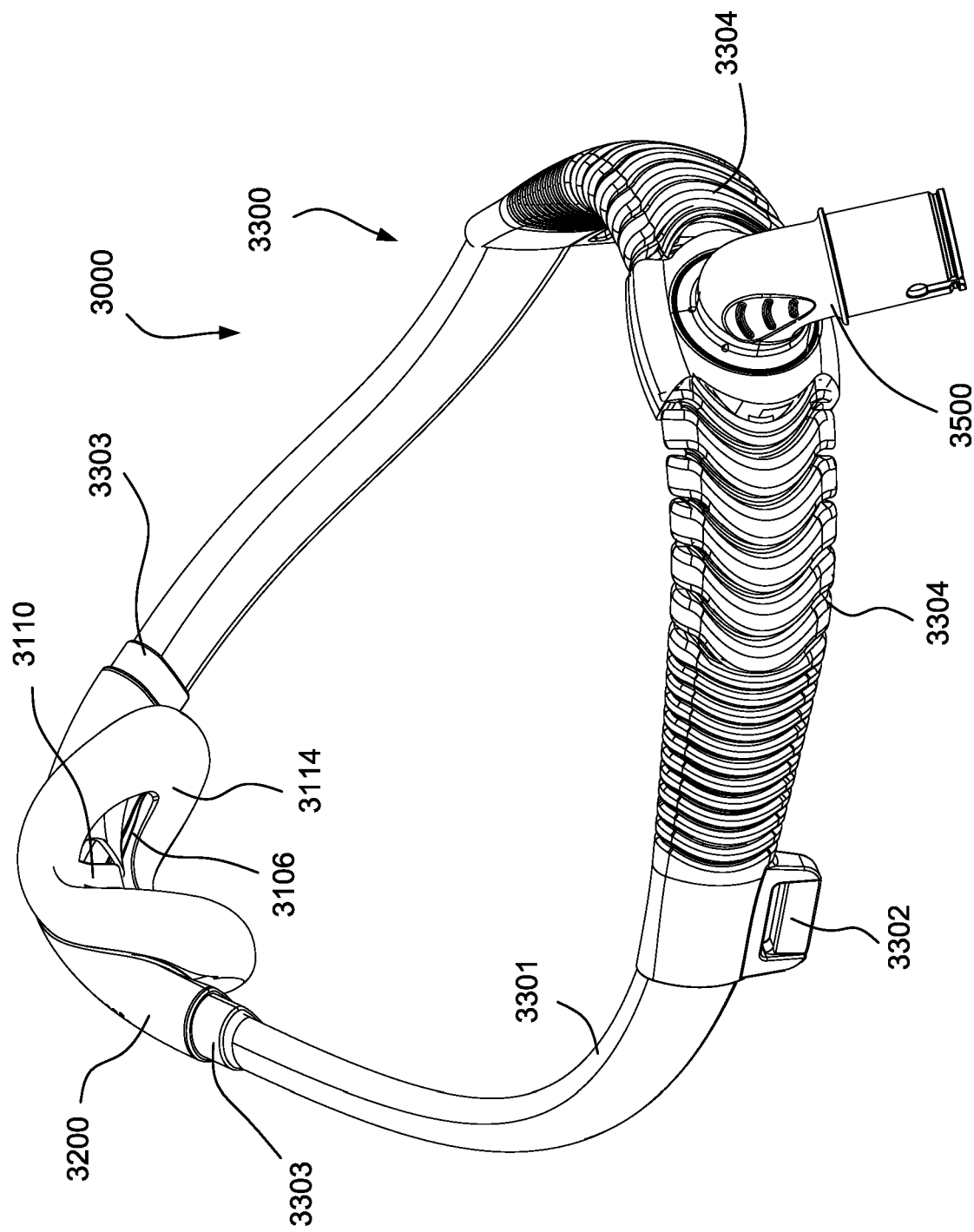

FIG. 10 depicts a superior perspective view of a patient interface according to an example of the present technology.

Figure 11:
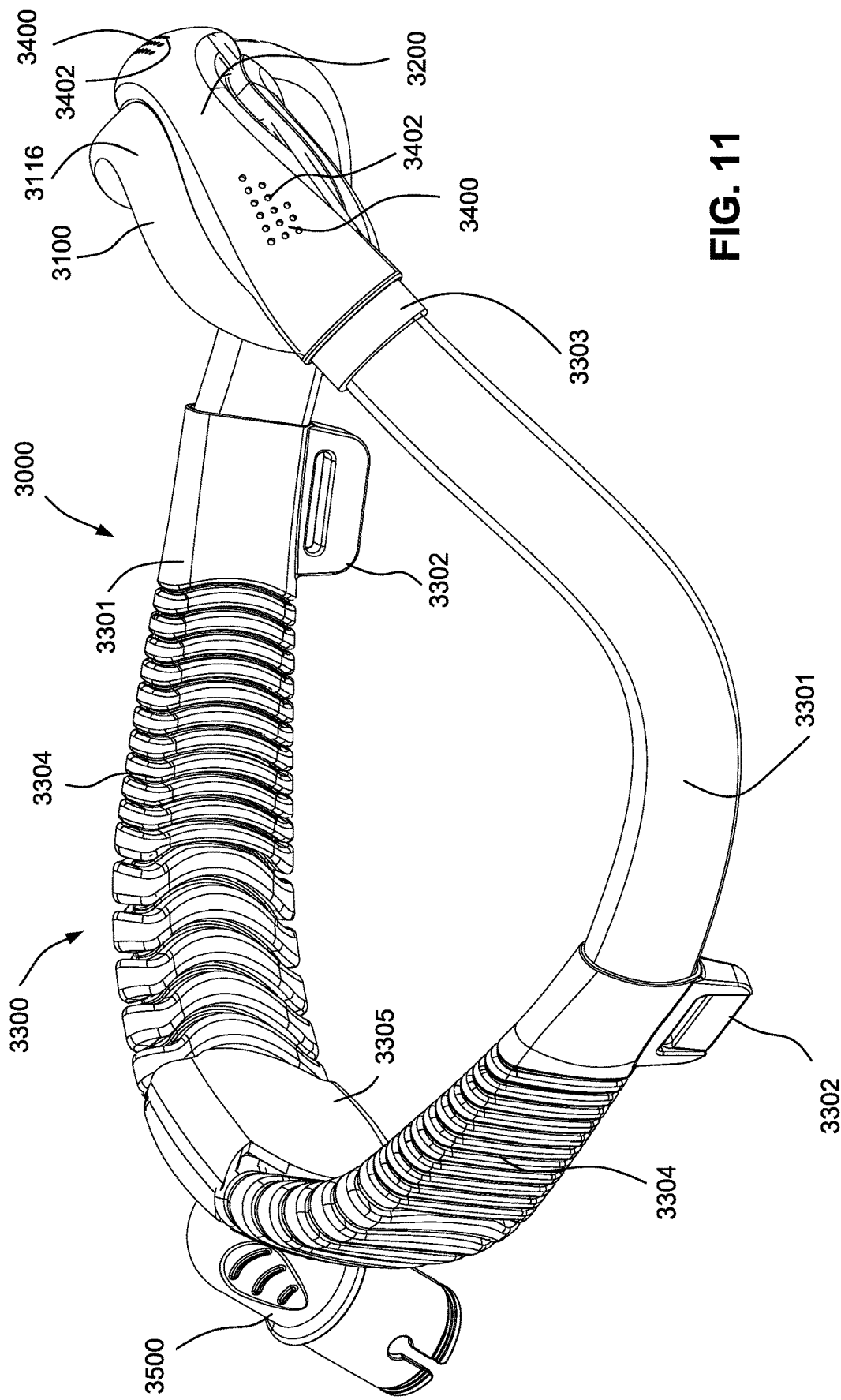

FIG. 11 depicts an anterior perspective view of a patient interface according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Seal-Forming Structure with Support Structure

FIGS. 7A to 7M depict a seal-forming structure 3100 according to an example of the present technology. The seal-forming structure 3100 may be characterized as a nasal cradle cushion. The seal-forming structure 3100 may be structured to seal with the patient's face around the patient's nares to provide the pressurized, breathable air to the patient's nasal airways while not covering the patient's mouth.

An inferior portion of the seal-forming structure 3100 may engage the patient's lip superior to form a seal, and the seal-forming structure 3100 may not extend beyond the lip superior to the patient's upper vermilion. In an example, a superior portion of the seal-forming structure 3100 may be structured to engage the patient's nose inferior to the patient's nasal bone to form a seal. In another example, a superior portion of the seal-forming structure 3100 may be structured to engage the patient's nose inferior to the patient's pronasale to form a seal. Lateral portions of the seal-forming structure 3100 may be structured to engage the patient's face between the patient's nasal alar and the patient's cheeks to form a seal. The lateral portions of the seal-forming structure 3100 may be structured to extend beyond the alar crest point to engage the patient's face and form a seal.

The seal-forming structure 3100 according to the present technology may include attributes of nasal cradle cushions disclosed in International Application Publication Nos. WO 2014/110626, filed Jan. 16, 2014, and WO 2015/070289, filed Nov. 14, 2014, each of which is incorporated herein by reference in its entirety.

The seal-forming structure 3100 according to the example depicted in FIGS. 7A to 7M includes a connection region 3102 at an anterior side thereof. The connection region 3102 is structured to connect the seal-forming structure 3100 to the plenum chamber 3200. The connection region 3102 provides an interface for engagement with the plenum chamber 3102. The connection region 3102 may connect with the plenum chamber 3200 via a mechanical connection such as a friction fit, a snap fit, or a mechanical interlock of corresponding overhanging portions. The connection region 3102 may provide a removable connection to the plenum chamber 3200. The removable connection allows the seal-forming structure 3100 to be removed for cleaning or replacement.

The connection region 3102 of this example surrounds an anterior opening 3104 or hole. The anterior opening 3104 may be in fluid communication with the plenum chamber 3200 to receive the flow of pressurized, breathable gas and exhaled gas from the patient may pass through the anterior opening 3104 to the plenum chamber 3200 to be exhausted by the vent 3400. The anterior opening 3104 in this example is also divided by an anterior tie 3108 that spans the anterior opening 3104 in a superior-inferior direction between an inferior portion of the connection region 3102 and a superior portion of the connection region 3102.

The seal-forming structure 3100 of this example also includes a non-patient contacting surface 3116 surrounding the connection region 3102. The non-patient contacting surface 3116 faces away from the patient's face and does not contact the patient's face in use. The non-patient contacting surface 3116 may also at least partly contact the plenum chamber 3200.

The seal-forming structure 3100 of this example also includes a patient-contacting surface 3114. The patient-contacting surface 3114 faces the patient's face in use. The patient-contacting surface 3114 may at least partially seal against the patient's facial skin in use. The patient-contacting surface 3114 is arranged such that the patient's facial skin contacts the patient-contacting surface 3114 in use. The patient's facial skin may contact only parts of the patient-contacting surface 3114 or the patient's facial skin may contact all of the patient-contacting surface 3114 in use. The patient-contacting surface 3114 may be adjacent to the non-patient contacting surface 3116. The patient-contacting surface 3114 may also be contiguous with the non-patient contacting surface 3116.

The seal-forming structure 3100 of this example also includes a gas chamber 3120 bounded at least partially by an interior surface 3112 of the seal-forming structure 3100. The gas chamber 3120 may be pressurized up to 30 cmH$_2$O by the pressurized, breathable gas received from the plenum chamber 3200 during use.

As can be seen in the posterior view of FIG. 7D, a posterior opening 3106 or hole is formed in the patient-contacting surface 3114. Pressurized, breathable gas in the gas chamber 3120 of the seal-forming structure 3100 is communicated to the patient's nares through the posterior opening 3106. Gas exhaled from the patient's nares is communicated through the posterior opening 3106 to the gas chamber 3120 to be exhausted via the vent 3400. The posterior opening 3106 may be a single opening formed in the patient-contacting surface 3114 or the posterior opening 3106 may be divided into two separate openings that each communicates with a corresponding naris of the patient. The posterior opening 3106 may be bounded by an edge 3118 of the patient-contacting surface 3114.

The seal-forming structure 3100 of this example also includes a support structure 3110 that can be seen in FIGS. 7C, 7J, and 7M. The support structure 3110 is connected to the anterior tie 3108 at one end, and the connection is with the surface of the anterior tie 3108 that faces the interior of the gas chamber 3120 or faces in a posterior direction relative to the seal-forming structure 3100. The other end of the support structure 3110 is connected to the patient-contacting surface 3114 at the edge 3118. As can be seen in the cross-sectional views of FIGS. 7G to 7K and 7M, a superior portion of the patient-contacting surface 3114 of the seal-forming structure 3100 is not supported by an undercushion. The patient-contacting surface 3114 of the seal-forming structure 3100 may be a single layer that engages the patient's nose proximate to the pronasale. The single layer of the seal-forming structure 3100 in this region may be more flexible as compared to a dual-wall arrangement, i.e., an arrangement with an undercushion, which may provide a more comfortable and effective seal for a wider range of nose shapes. However, such a single layer arrangement may be more prone to blowout, e.g., where the pressurized, breathable gas causes the patient-contacting surface 3114 of the seal-forming structure 3100 to disengage from the patient's nose. The support structure 3110 counteracts this effect by tying the edge 3118 of the patient-contacting surface 3114 to another portion of the seal-forming structure 3100.

The support structure 3110 may be adjacent to or partially contact the patient's columella to prevent the patient's nose from protruding into the gas chamber 3120 of the seal-forming structure 3100. Depending on the size and shape of an individual patient's nose, the support structure 3110 may be near but not in direct contact with the patient's columella. The support structure 3110 may also support the patient-contacting surface 3114 and urge the patient-contacting surface 3114 into engagement with the patient's nose proximate to the pronasale to ensure effective sealing. FIG. 7J, for example, also shows that the support structure 3110 does not span the posterior opening 3106 and does not extend between a superior portion and an inferior portion of the edge 3118.

The support structure 3110 may have a different thickness than the patient-contacting surface 3114. The support structure 3110 may be thicker than the patient-contacting surface 3114. The support structure 3110 may have a variable thickness in a longitudinal direction. The support structure 3110 may have an increased thickness adjacent the one or both of the locations at which the support structure 3110 is joined to the seal-forming structure 3100.

The support structure 3110 may, along with the interior surface 3112 and the anterior tie 3108 of the seal-forming structure 3100, form a continuous loop, as can be seen in FIG. 7G. In an alternative example, the support structure 3110 may be connected to the interior surface 3112 of the seal-forming structure 3100 and not to the anterior tie 3108. In such an alternative example, the anterior tie 3108 may be omitted. The support structure 3110 may have a length in an undeformed state that is greater than a linear distance from the two locations at which the support structure 3110 connects to the seal-forming structure 3110 to provide a degree of slack in the support structure.

FIG. 7G also shows that the support structure 3110 is curved slightly inward into the gas chamber 3120 in an undeformed state. This curvature may allow the support structure 3110 to better accommodate the patient's nose, including the pronasale. Alternatively, the support structure 3110 may be straight in an undeformed state of another example. Additionally, FIG. 7G shows that the patient-contacting surface 3114 is contiguous with an external or posterior surface of the support structure 3110. In an alternative example, the support structure 3110 may be connected to the interior surface 3112 of the seal-forming structure 3100 opposite the patient-contacting surface 3114 such that the edge 3118 separates the patient-contacting surface 3114 and the support structure 3110.

The seal-forming structure 3100, particularly the support structure 3110, may include attributes of the tie 3110 disclosed by International Application Publication No. WO 2016/149769, filed Mar. 24, 2016, which is incorporated herein by reference in its entirety.

The seal-forming structure 3100 may also include an undercushion 3122 that supports a portion of the patient-contacting surface 3114, as can be seen in FIGS. 7G to 7M. The undercushion 3122 may only support an inferior portion of the undercushion 3122. The undercushion 3122 may be provided to only the lower half of the seal-forming structure 3100. The undercushion 3122 of these examples may be configured to support the patient-contacting surface 3114 against the patient's lip superior to ensure an effective seal. A similar undercushion layer 3105 is disclosed by U.S. Provisional Application No. 62/328,988, filed Apr. 28, 2016, which is incorporated herein by reference in its entirety.

The connection region 3102 of the seal-forming structure 3100 may have a shape that resembles an infinity loop (∞) or the number eight (8). It may also be described as having an "hour-glass" shape. The connection region 3102 may be shaped such that its narrowest point is at the centreline of the seal-forming structure 3100. The connection region 3102 may then widen in the superior-inferior direction in either lateral direction away from the centreline, e.g., as shown in FIG. 7B.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

The vent 3400 provided to the plenum chamber 3200 may include a plurality of openings 3402. The openings 3402 may be arranged in two groups that are symmetrical relative to the centreline of the plenum chamber 3200. The plurality of openings 3402 may reduce noise and diffuse the vent flow concentration.

The openings 3402 may be located sufficiently close to the centreline of the plenum chamber 3200 such that the openings 3402 are not blocked when the patient is sleeping on their side. To avoid weakening the chassis at a relatively narrow portion, the openings 3402 may be spaced from the centreline.

The openings 3402 may have a circular profile.

5.3.5 Decoupling Structure(s)

In one form the patient interface 3000 includes at least one decoupling structure 3500, for example, a swivel or a ball and socket. FIGS. 8A, 8B, 9A, and 9B depict examples of decoupling structures 3500 according to examples of the present technology. The decoupling structures 3500 may be in the form of an elbow. The decoupling structures 3500 may include a swivel 3501 that connects to the air circuit 4170 and a patient interface connector 3502 that connects to the patient interface 3000. The patient interface connector 3502 may permit the tube 3503 of the decoupling structure 3500 to rotate relative to the patient interface 3500. The decoupling structure 3500 may also include a vent 3400. The vent 3400 of the decoupling structure 3500 may include at least one opening 3401 through a portion of the tube 3503 and/or through a portion of the patient interface connector 3502.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.3.10 Patient Interface of the Present Technology

FIGS. 10 and 11 depict a patient interface 3000 according to an example of the present technology. The patient interface 3000 includes the seal-forming structure 3100 according to the examples described in section 4.3.1 above. The seal-forming structure 3100 may be connected to the plenum chamber 3200 as described above as well. The plenum chamber 3200 may be provided with one or more vents 3400.

The patient interface 3000 may include a positioning and stabilising structure 3300 that includes conduits 3301. The conduits 3301 serve two purposes: 1) to position and stabilize the patient interface 3000 on the patient's head in a therapeutically effective position during use and 2) to provide the pressurized, breathable gas to the plenum chamber 3200. As such, the conduits 3301 may be constructed of a flexible, biocompatible material and may also form a hollow structure. The conduits 3301 may be connected to the plenum chamber 3200 with clips 3303 to provide a pneumatic connection therebetween. The conduits 3301 may also include strap connectors 3302 to connect to a strap (not shown) that passes behind the patient's head in use. The conduits 3301 may also include flexible portions 3304 that provide flexibility to the conduits 3301 to accommodate different sizes and shapes of patient heads. An elbow connector 3305

5.4 RPT Device

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor in accordance with the present technology may be based on a differential pressure transducer, for example, an SDP600 Series differential pressure transducer from SENSIRION.

In one form, a signal representing a flow rate from the flow rate sensor is received by the central controller.

5.4.1.4.2 Pressure Sensor

A pressure sensor in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor is received by the central controller.

5.4.1.4.3 Motor Speed Transducer

In one form of the present technology a motor speed transducer is used to determine a rotational velocity of the motor 4144 and/or the blower 4142. A motor speed signal from the motor speed transducer may be provided to the therapy device controller. The motor speed transducer may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller.

In one form, the input device 4220 may be constructed and arranged to allow a person to select a value and/or a menu option.

5.4.2.3 Central Controller

In one form of the present technology, the central controller is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers 4270, one or more input devices 4220, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.8.4 Anatomy 5.8.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Midsagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List

| | |
|---|---|
| patient | 1000 |
| bed partner | 1100 |
| patient interface | 3000 |
| seal - forming structure | 3100 |
| connection region | 3102 |
| anterior opening | 3104 |
| posterior opening | 3106 |
| anterior tie | 3108 |
| support structure | 3110 |
| interior surface | 3112 |
| patient contacting surface | 3114 |
| non-patient contacting surface | 3116 |
| edge | 3118 |
| gas chamber | 3120 |
| undercushion | 3122 |
| plenum chamber | 3200 |
| chord | 3210 |
| superior point | 3220 |
| inferior point | 3230 |
| positioning and stabilising structure | 3300 |
| conduit | 3301 |
| strap connector | 3302 |
| clip | 3303 |
| flexible portion | 3304 |
| elbow connector | 3305 |
| vent | 3400 |
| opening | 3401 |
| opening | 3402 |
| decoupling structure | 3500 |
| swivel | 3501 |
| patient interface connector | 3502 |
| tube | 3503 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| supplemental oxygen | 4180 |
| electrical components | 4200 |
| PCBA | 4202 |
| power supply | 4210 |
| input device | 4220 |
| transducer | 4270 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |

The invention claimed is:

1. A patient interface comprising:
a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient,
a seal-forming structure constructed and arranged to form a seal with a region of the patient's face surrounding an entrance to the patient's airways, the seal-forming structure constructed and arranged to maintain said therapeutic pressure in the plenum chamber throughout the patient's respiratory cycle in use;
a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and
a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered, wherein the seal-forming structure further comprises a patient-contacting surface configured to engage the patient's facial skin to form a seal and a posterior opening formed in the patient-contacting surface, the posterior opening configured to provide the flow of air at said therapeutic pressure to the patient's nares, and wherein the seal-forming structure includes a support structure extending from a first location on the patient contacting surface to a second location on an interior surface of the seal-forming structure, the support structure and the interior surface forming a continuous loop, and wherein a superior portion of the seal-forming structure is structured to engage the patient's nose inferior to the patient's nasal bone.

2. The patient interface of claim 1, wherein the seal-forming structure further comprises an anterior opening formed in a non-patient contacting surface and an anterior tie that spans the anterior opening, and wherein a first end of the support structure is connected to the anterior tie.

3. The patient interface of claim 2, wherein the seal-forming structure further comprises an edge bounding the posterior opening in the patient contacting surface, and wherein a second end of the support structure is connected to the patient contacting surface at a superior region of the edge.

4. The patient interface of claim 1, wherein the support structure has a length in an undeformed state that is greater than a linear distance from the first location to the second location.

5. The patient interface of claim 1, wherein the support structure is configured to be positioned adjacent to or in contact with the patient's columella during use.

6. The patient interface of claim 1, wherein the support structure is curved along a longitudinal axis of the support structure in an undeformed state.

7. The patient interface of claim 1, wherein the support structure has a different thickness than the patient-contacting surface.

8. The patient interface of claim 1, wherein the support structure is thicker than the patient-contacting surface.

9. The patient interface of claim 1, wherein the support structure does not extend completely across the posterior opening.

10. The patient interface of claim 1, wherein the seal-forming structure at least partly forms a gas chamber, and wherein in an undeformed state the support structure extends into the gas chamber.

11. The patient interface of claim 1, wherein the support structure has a variable thickness in a longitudinal direction.

12. The patient interface of claim 1, wherein the support structure has an increased thickness adjacent the first location and/or the second location.

13. The patient interface of claim 1, wherein a portion of the support structure is curved away from the patient's nose along a longitudinal axis of the support structure in an undeformed state.

14. The patient interface of claim 1, wherein the seal-forming structure further comprises an undercushion that supports the patient contacting surface.

15. The patient interface of claim 14, wherein an inferior portion of the seal-forming structure includes the undercushion and the superior portion of the seal-forming structure does not include the undercushion.

16. The patient interface of claim 14, wherein the undercushion is structured to only support the patient contacting surface against the patient's lip superior.

17. The patient interface of claim 1, wherein the superior portion of the seal-forming structure is structured to engage the patient's nose inferior to the patient's pronasale.

18. The patient interface of claim 1, wherein an inferior portion of the seal-forming structure is structured to engage the patient's lip superior such that the seal-forming structure does not extend beyond the lip superior to the patient's upper vermilion.

* * * * *